US010199728B2

(12) United States Patent
Hong et al.

(10) Patent No.: US 10,199,728 B2
(45) Date of Patent: Feb. 5, 2019

(54) APPARATUS FOR SIGNAL RADIATION IN TRANSMISSION DEVICE

(71) Applicant: Samsung Electronics Co., Ltd., Suwon-si, Gyeonggi-do (KR)

(72) Inventors: Won-Bin Hong, Seoul (KR); Yoon-Geon Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 57 days.

(21) Appl. No.: 15/310,312

(22) PCT Filed: May 12, 2015

(86) PCT No.: PCT/KR2015/004759
§ 371 (c)(1),
(2) Date: Nov. 10, 2016

(87) PCT Pub. No.: WO2015/174723
PCT Pub. Date: Nov. 19, 2015

(65) Prior Publication Data
US 2017/0141466 A1 May 18, 2017

(30) Foreign Application Priority Data

May 12, 2014 (KR) .................. 10-2014-0056546
May 12, 2015 (KR) .................. 10-2015-0066086

(51) Int. Cl.
*H01Q 1/38* (2006.01)
*H01Q 5/28* (2015.01)
(Continued)

(52) U.S. Cl.
CPC .............. *H01Q 5/28* (2015.01); *H01Q 1/243* (2013.01); *H01Q 3/24* (2013.01); *H01Q 5/335* (2015.01);
(Continued)

(58) Field of Classification Search
CPC .......... H01Q 13/06; H01Q 1/243; H01Q 1/46; H01Q 5/28; H01Q 5/335; H01Q 1/38
See application file for complete search history.

(56) References Cited

U.S. PATENT DOCUMENTS 2,887,683 A * 5/1959 Edwin Dyke .......... H01Q 19/12
343/772
3,771,077 A 11/1973 Tischer
(Continued)

FOREIGN PATENT DOCUMENTS

DE 19958750 A1 7/2001
JP 2003060431 A 2/2003
(Continued)

OTHER PUBLICATIONS

European Search Report dated Dec. 14, 2017, issued in the European Patent Application No. 15792557.9-1927.
(Continued)

*Primary Examiner* — Tho G Phan
(74) *Attorney, Agent, or Firm* — Jefferson IP Law, LLP

(57) ABSTRACT

The present disclosure relates to a pre-$5^{th}$-Generation (5G) or 5G communication system to be provided for supporting higher data rates Beyond $4^{th}$-Generation (4G) communication system such as Long Term Evolution (LTE). The present invention relates to an antenna structure for signal radiation in a transmission device. An apparatus for signal radiation includes a feeding unit configured to radiate a signal, and a guiding unit, that consists of a plurality of elements physically spaced from one another, configured to adjust a radiation pattern of the signal radiated by the feeding unit by generating a radio wave in a Transverse Electric (TE) mode. Further, the present invention also includes embodiments different from the above-described embodiment.

20 Claims, 25 Drawing Sheets

(51) Int. Cl.
*H01Q 3/24* (2006.01)
*H01Q 21/06* (2006.01)
*H01Q 5/335* (2015.01)
*H01Q 1/24* (2006.01)
*H01Q 13/28* (2006.01)
*A61B 8/00* (2006.01)

(52) U.S. Cl.
CPC ........... *H01Q 13/28* (2013.01); *H01Q 21/067* (2013.01); *H01Q 21/068* (2013.01); *A61B 8/4472* (2013.01)

(56) References Cited

U.S. PATENT DOCUMENTS

| | | | |
|---|---|---|---|
| 5,220,335 A * | 6/1993 | Huang | H01Q 1/38 343/700 MS |
| 6,326,922 B1 * | 12/2001 | Hegendoerfer | H01Q 1/38 343/700 MS |
| 7,015,860 B2 | 3/2006 | Alsliety | |
| 7,088,300 B2 | 8/2006 | Fisher | |
| 8,022,887 B1 | 9/2011 | Zarnaghi | |
| 9,734,989 B2 * | 8/2017 | Kodaira | H01J 37/321 |
| 9,905,921 B2 * | 2/2018 | Sazegar | H01Q 3/24 |
| 2003/0098815 A1 | 5/2003 | Teshirogi et al. | |

FOREIGN PATENT DOCUMENTS

| | | |
|---|---|---|
| JP | 2006197370 A | 7/2006 |
| JP | 2009182580 A | 8/2009 |
| JP | 2010050700 A | 3/2010 |
| JP | 2010193052 A | 9/2010 |

OTHER PUBLICATIONS

Chinese Notification of the First Office Action dated Sep. 30, 2018, issued in the Chinese Application No. 201580026194.5.

* cited by examiner

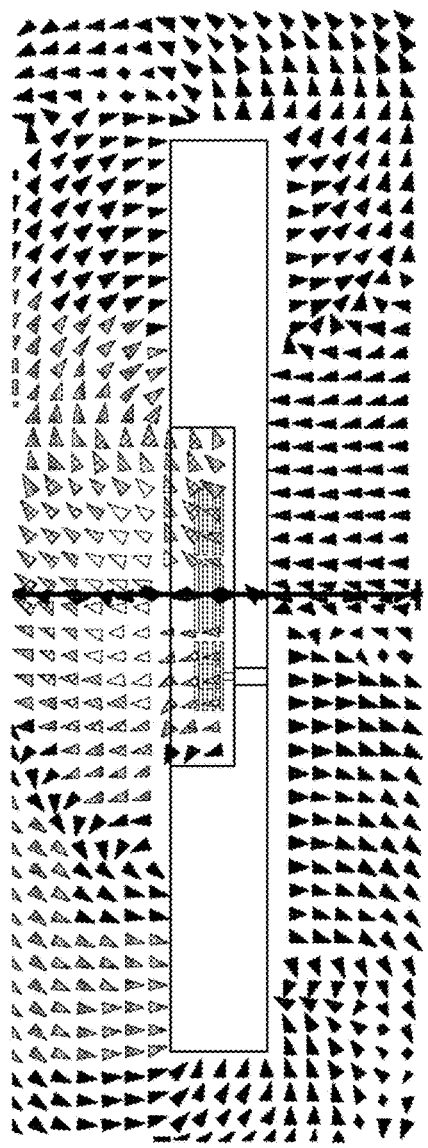
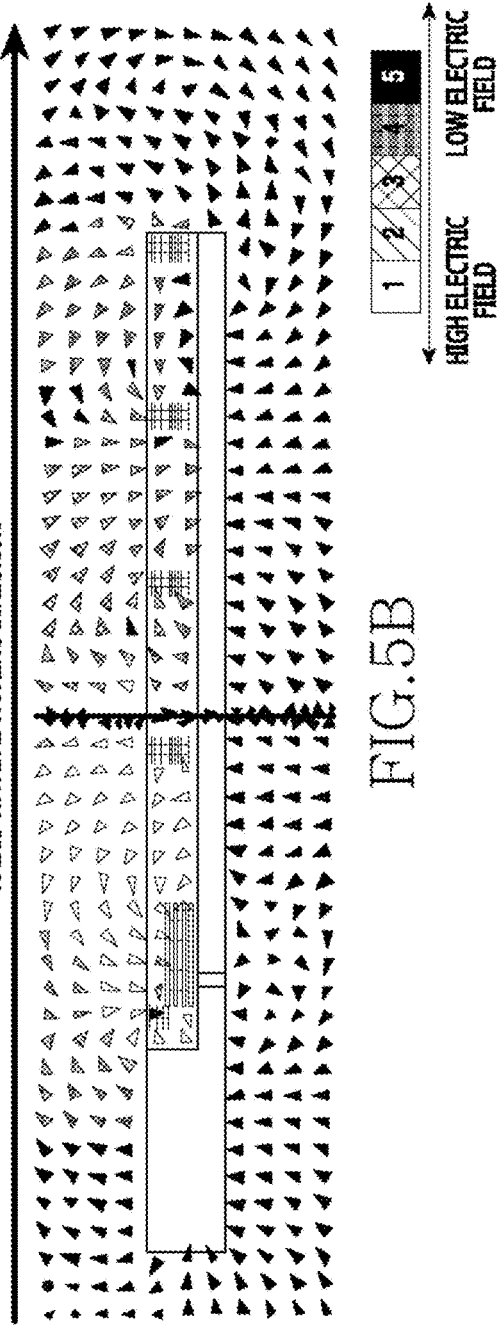
FIG.5A
FIG.5B (a)

(b)

APPARATUS FOR SIGNAL RADIATION IN TRANSMISSION DEVICE

TECHNICAL FIELD

The present invention relates to an antenna of a wireless transmission device.

BACKGROUND ART

To meet the demand for wireless data traffic having increased since deployment of $4^{th}$ generation (4G) communication systems, efforts have been made to develop an improved $5^{th}$ generation (5G) or pre-5G communication system. Therefore, the 5G or pre-5G communication system is also called a 'Beyond 4G Network' or a 'Post Long Term Evolution (LTE) System'.

The 5G communication system is considered to be implemented in higher frequency (mmWave) bands, e.g., 60 GHz bands, so as to accomplish higher data rates. To decrease propagation loss of the radio waves and increase the transmission distance, the beamforming, massive multiple-input multiple-output (MIMO), Full Dimensional MIMO (FD-MIMO), array antenna, an analog beam forming, large scale antenna techniques are discussed in 5G communication systems.

In addition, in 5G communication systems, development for system network improvement is under way based on advanced small cells, cloud Radio Access Networks (RANs), ultra-dense networks, device-to-device (D2D) communication, wireless backhaul, moving network, cooperative communication, Coordinated Multi-Points (CoMP), reception-end interference cancellation and the like.

In the 5G system, Hybrid frequency shift keying (FSK) and quadrature amplitude modulation (FQAM) and sliding window superposition coding (SWSC) as an advanced coding modulation (ACM), and filter bank multi carrier (FBMC), non-orthogonal multiple access (NOMA), and sparse code multiple access (SCMA) as an advanced access technology have been developed.

In addition, thanks to the development of technology, communication devices are miniaturized and various electronic devices are providing services based on a network using the communication devices. Accordingly, related-art devices which do not have communication functions mounted therein as well as mobile terminals (for example, cellular phones, smart phones, or the like) which are manufactured for the purpose of communication are providing various services using communication. In this case, it is common that wireless communication technology is applied in order to provide convenience of portability and avoid inconvenience caused by wire communication.

For wireless communication, an antenna for radiating a signal should be included. In order to transmit a signal through an antenna, a transmission device generates a baseband signal from transmission data and generates a Radio Frequency (RF) through a Radio Frequency Integrated Circuit (RFIC).

The RFIC and the antenna are normally connected with each other through a transmission line. However, the transmission of the signal through the transmission line may cause loss of a transmission signal. The loss of the transmission signal may reduce an antenna gain and eventually may cause deterioration of performance of the system.

DETAILED DESCRIPTION OF THE INVENTION

Technical Objects

An exemplary embodiment of the present invention provides an apparatus for enhancing an antenna gain in a wireless transmission device.

Another exemplary embodiment of the present invention provides an apparatus for reducing loss which is caused by a transmission line in a wireless transmission device.

Another exemplary embodiment of the present invention provides an antenna apparatus which has a minimized transmission line in a wireless transmission device.

Technical Solving Means

According to an exemplary embodiment of the present invention, an apparatus for signal radiation includes: a feeding unit which radiates a signal; and a guiding unit that consists of a plurality of elements physically spaced from one another, and adjusts a radiation pattern of the signal radiated by the feeding unit.

According to an exemplary embodiment of the present invention, a method for operating of a transmission device includes: radiating a signal; and adjusting a radiation pattern of the signal through a guiding unit which is formed of a plurality of elements physically spaced from one another.

Advantageous Effect

Through a structure in which a transmission line between a Radio Frequency Integrated Circuit (RFIC) and an antenna is removed in a wireless transmission device, an antenna gain can be enhanced.

BRIEF DESCRIPTION OF THE DRAWINGS

FIGS. 5A and 5B illustrate a radio wave advancing direction and an electric field which are caused by an antenna in a transmission device according to an exemplary embodiment of the present invention;

BEST MODE FOR EMBODYING THE INVENTION

Operation principles of the present invention will be described in detail herein below with reference to the accompanying drawings. In the following description, well-known functions or constructions are not described in detail since they would obscure the invention in unnecessary detail. Also, the terms used herein are defined according to the functions of the present invention. Thus, the terms may vary depending on user's or operator's intension and usage. That is, the terms used herein must be understood based on the descriptions made herein.

Hereinafter, the present invention will be described regarding technology for signal radiation in a wireless transmission device. A term indicating a component of an antenna, which is used in the following description, a term for explaining a radio wave characteristic, or the like are just for the convenience of explanation. Therefore, the present invention is not limited to the terms described below and other terms indicating an object having the same technical meaning may be used.

In the present invention, the wireless transmission device may be a portable electronic device, and may be a communicating means which is included in one of a smart phone, a portable terminal, a mobile phone, a mobile pad, a media player, a tablet computer, a handheld computer, or a Personal Digital Assistant (PDA). In addition, the wireless transmission device may be a communicating means for a device which combines the functions of two or more of the above-mentioned devices.

Figure 1:
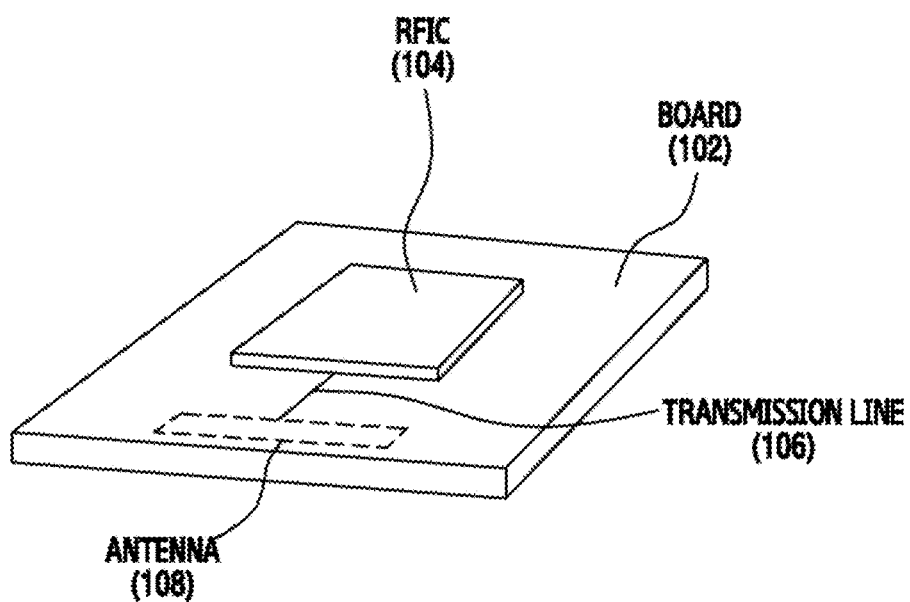
FIG. 1 illustrates an example of a connection structure of a Radio Frequency Integrated Circuit (RFIC) and an antenna in a transmission device.

A structure of a device including a normal antenna is as illustrated in FIG. 1. FIG. 1 illustrates an example of a connection structure of a Radio Frequency Integrated Circuit (RFIC) and an antenna in a transmission device. An example of the connection structure of the RFIC and the antenna is as illustrated in FIG. 1. Referring to FIG. 1, an RFIC 104 is installed on a board 102 and an antenna 108 is arranged in the proximity of a corner of the board 102. Furthermore, the RFIC 104 and the antenna 108 are connected with each other through a transmission line 106 in order to transmit an RF signals from the RFIC 104 to the antenna 108.

Figure 2:
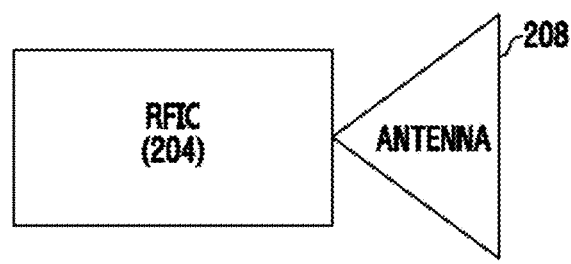
FIG. 2 illustrates a connection structure of an RFIC and an antenna in a transmission device according to an exemplary embodiment of the present invention.

However, the loss of a transmission signal may be caused by the transmission of the signal through the transmission line. The loss of the transmission signal may reduce an antenna gain and eventually may cause deterioration of performance of a system. Accordingly, the present invention suggests a connection structure of an RFIC and an antenna of a structure as shown in FIG. 2. FIG. 2 illustrates a connection structure of an RFIC and an antenna in a transmission device according to an exemplary embodiment of the present invention.

Referring to FIG. 2, the RFIC 204 and the antenna 208 of the transmission device are connected with each other without a transmission line. That is, in order to reduce loss caused by the transmission of a signal through the transmission line, the transmission device according to exemplary embodiments of the present invention includes the connection structure of the RFIC 204 and the antenna 208 in which the transmission line is removed or minimized. The RFIC 204 is a means for performing processing, such as amplifying, filtering, or the like, with respect to an RF signal, and may be referred as a different name. For example, the RFIC 204 may be referred to as a transceiver, an RF processor, or the like.

According to an exemplary embodiment of the present invention, the antenna 208 may have a shape formed by simply removing a transmission line from a related-art antenna. According to another exemplary embodiment of the present invention, the antenna 208 may further include components for controlling performance of signal radiation in a space where the transmission line is to be disposed, in addition to the shape formed by simply removing the transmission line from the related-art antenna.

Figure 3:
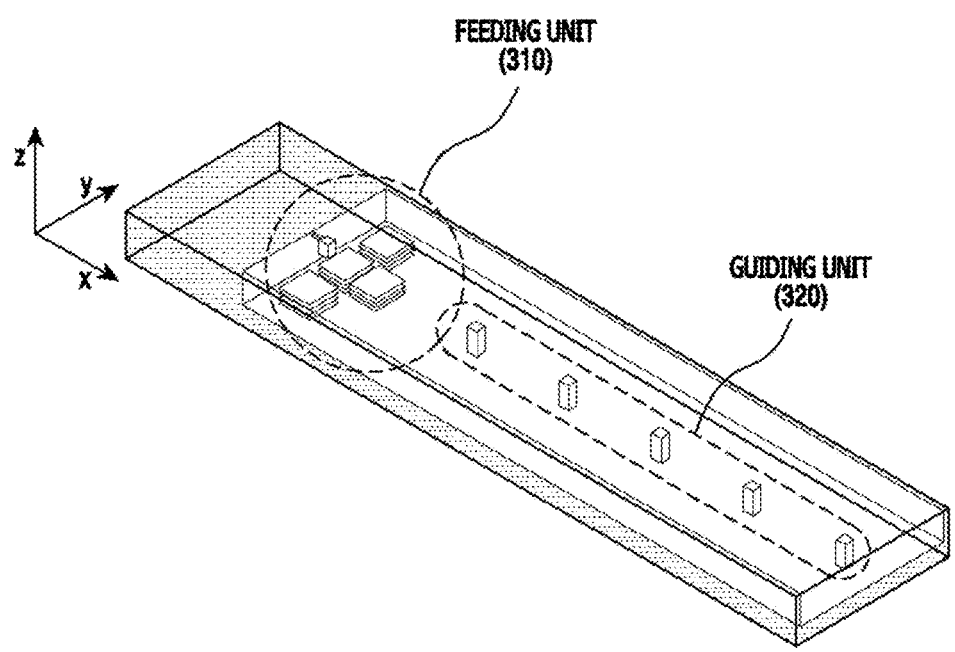
FIG. 3 illustrates a configuration example of an antenna in a transmission device according to an exemplary embodiment of the present invention.

FIG. 3 illustrates a configuration example of an antenna in a transmission device according to an exemplary embodiment of the present invention.

Referring to FIG. 3, the antenna includes a feeding unit 310 and a guiding unit 320.

The feeding unit 310 receives an RF signal from an RFIC and radiates the RF signal. The feeding unit 310 performs impedance matching with the antenna. The RF signal from the RFIC may be inputted to the feeding unit 310 through physical connection. That is, the feeding unit 310 may be connected with the RFIC without an extra transmission line. Alternatively, the feeding unit 310 may be connected with the RFIC through a transmission line having a length which is shorter than a threshold. In the case of FIG. 3, the feeding unit 310 is illustrated as including a plurality of sub units. However, the structure of the feeding unit 310 illustrated in FIG. 3 is merely an example and the feeding unit 310 may have a different structure.

The guiding unit 320 radiates the signal radiated from the feeding unit 310 to the outside in a desired radiation pattern. That is, the signal radiated from the feeding unit 310 is radiated to the outside of the transmission device through the guiding unit 320. In this case, the radiation pattern may vary according to a detailed structure of the guiding unit 320. The guiding unit 320 is formed of a plurality of guide elements and the guide elements are arranged in a predetermined direction. The guide elements are physically spaced from one another, and a distance between neighbor guide elements may be regular or irregular, or may be substantially regular within a pre-defined error range.

Figure 4A:
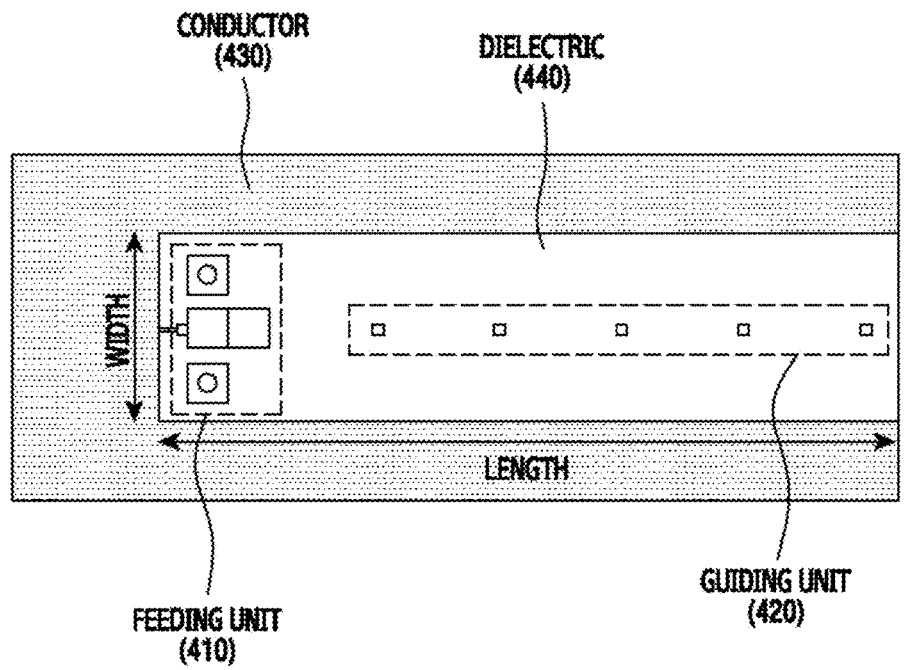
FIGS. 4A and 4B illustrate a criterion for measuring of an antenna in a transmission device according to an exemplary embodiment of the present invention.
Figure 4B:
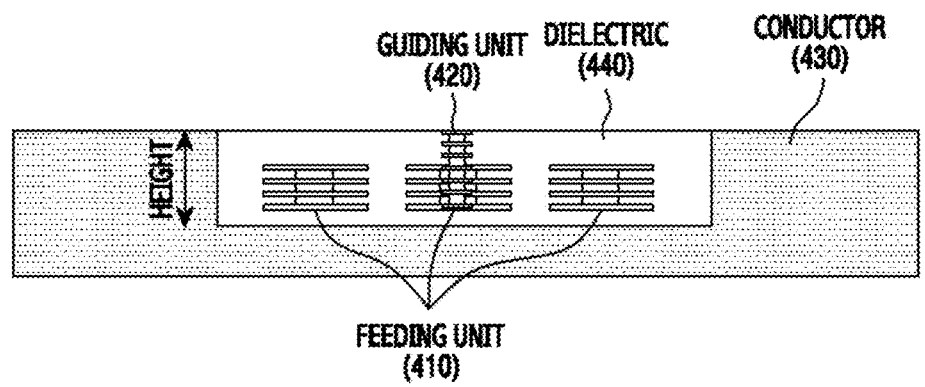

FIGS. 4A and 4B illustrate a criterion for measuring of an antenna in a transmission device according to an exemplary embodiment of the present invention. FIG. 4A illustrates a plane view of the antenna and FIG. 4B illustrates a front view of the antenna.

Referring to FIGS. 4A and 4B, a feeding unit 410 and a guiding unit 420 are disposed in a dielectric 440. The feeding unit 410 and the guiding unit 420 may be disposed in the form of connection to the inside of the dielectric 440, or the dielectric 440 may be installed in the form of a cover which is placed above the feeding unit 410 and the guiding unit 420. In this case, as shown FIG. 4B, some of the guide elements of the guiding unit 420 may be exposed to the outside of the dielectric 440. The dielectric 440 may be configured by at least one of a Printed Circuit Board (PCB), silicon, Low Temperature Co-fired Ceramics (LTCC), Liquid Crystal Polymer (LCP).

As shown in FIG. 4A, the dielectric 440 is enclosed by a conductor 430 on the plane view. In addition, as shown in FIG. 4B, one surface of the dielectric 440 may not be enclosed by the conductor 430 and may be opened. That is, some of the surfaces parallel to the longitudinal direction of the guiding unit 420 are shielded by the conductor 430 and the other surfaces are opened. For example, the opened surface may include a surface through which the guide elements of the guiding unit 420 are exposed to the outside of the dielectric 440.

In the above-described structure, a size of the dielectric 440 on the x-axis is designated as a length, and a size on the y-axis is designated as a width as shown in FIG. 4A. In addition, as shown in FIG. 4B, a size of the dielectric on the z-axis is designated as a height. The definition of the length, the width, and the height is merely an example for the convenience of explanation. Accordingly, the definition of the length, the width, and the height may be modified or changed according to an intention of a practicer of the present invention.

FIGS. 5A and 5B illustrate a radio wave advancing direction and an electric field which are caused by the antenna in the transmission device according to an exemplary embodiment of the present invention. FIG. 5A illustrates an electric field which is observed on the x-y plane corresponding to the front view of the antenna, and FIG. 5B illustrates an electric field which is observed on the x-z plane corresponding to the side view of the antenna.

Referring to FIGS. 5A and 5B, the antenna according to an exemplary embodiment of the present invention generates a radio wave of a Transverse Electric (TE) mode. The TE mode refers to a polarization form which is classified into linear polarization with a Transverse Magnetic (TM) mode, Transverse Electric Magnetic (TEM). The TE mode means linear polarization in which the electric field is perpendicular to the advancing direction of the radio wave. That is, in the antenna according to an exemplary embodiment of the present invention, the electric field is generated perpendicular to the radio wave advancing direction. In this case, an equation regarding the radio wave is as shown in Equation 1 presented below:

$$\left(\frac{\partial^2}{\partial x^2} + \frac{\partial^2}{\partial y^2} + \frac{\partial^2}{\partial z^2} + k^2\right) Hz = 0, \; Hz = h_z(x, y)e^{-j\beta z} \quad \text{Equation 1}$$

In equation 1, k is a propagation constant, Hz is an z-axis value of a magnetic field, $h_z$ is an amplitude of the z-axis value of the magnetic field, $\beta_z$ is a phase constant which advances on the z-axis.

Figure 6:
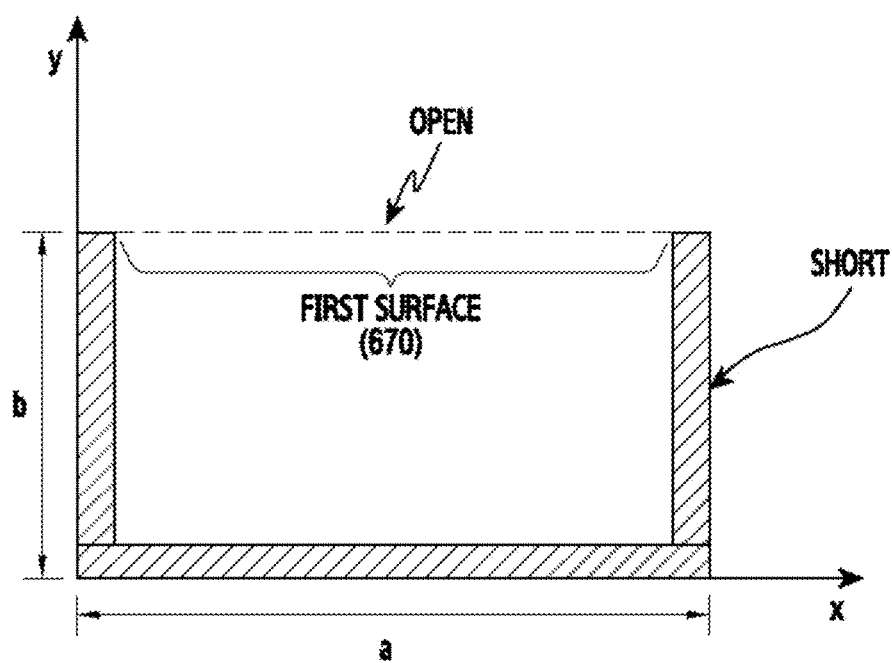
FIG. 6 illustrates a structure of an antenna for controlling a polarization characteristic in a transmission device according to an exemplary embodiment of the present invention.

FIG. 6 illustrates a structure of an antenna for controlling a polarization characteristic in a transmission device according to an exemplary embodiment of the present invention. FIG. 6 illustrates a simplified structure of the antenna corresponding to the front view of the antenna. In FIG. 6, the x-axis and the y-axis are different from the x-axis and the y-axis defined in FIG. 3, and the x-axis of FIG. 6 is consistent with the y-axis of FIG. 3 and the y-axis of FIG. 6 is consistent with the z-axis of FIG. 3.

Referring to FIG. 6, three surfaces except for a first surface 670 out of the four surfaces of the antenna are in a short state, and the first surface is opened. That is, the three of the four surfaces of the antenna are shielded by the conductor, and the other surface, the first surface 670, is opened. In this case, a boundary condition is as shown in Equation 2 presented below:

$$\begin{cases} if e_x = 0, & y = 0 \\ if e_x = T, & y = 0 \end{cases} \quad \text{Equation 2}$$

$$\begin{cases} if e_y = 0, & x = 0 \\ if e_y = 0, & x = \alpha \end{cases}$$

In equation 2, $e_x$ is an x-axis component of the electric field, y is a size of the antenna in a height direction, $e_y$ is an y-axis component of the electric field, and x is a size of the antenna in a width direction.

In addition, an example of a condition of the size of the antenna in the height direction and the size in the width direction according to a frequency of a transmission signal is as shown in Equation 3 presented below, for example:

$$k_c^2 = k_x^2 + k_y^2 = -\beta^2 + k^2 \quad \text{Equation 3}$$

$$f_c = \frac{1}{2\Pi\sqrt{\mu\varepsilon}}\sqrt{\left(\frac{m\Pi}{a}\right)^2 + \left(\frac{(2n+1)\Pi}{2b}\right)^2}$$

In equation 3, $k_c$ is a propagation constant of a cutoff frequency band, $k_x$ is an x-axis component of the propagation constant, $k_y$ is a y-axis component of the propagation constant, $\beta$ is a phase constant of a radio wave advancing direction, k is a propagation constant, $f_c$ is a frequency of a transmission signal, $\Pi$ is pi, $\mu$ is permeability of an inner medium of the antenna, $\varepsilon$ is permittivity of the inner medium of the antenna, a is a size of the antenna in the width direction, n is a certain natural number, and b is a size of the antenna in the height direction.

The TE mode may be divided into a $TE_{10}$ mode and a $TE_{01}$ mode. The $TE_{10}$ mode and the $TE_{01}$ mode are divided according to a length of a cutoff wave length, and the $TE_{10}$ mode is a mode in which the cutoff wave length is two times longer than the size of the antenna in the width direction, and $TE_{01}$ mode is a mode in which the cutoff wave length is two times longer than the size of the antenna in the height direction. When Equation 3 is rearranged, the frequency in the $TE_{10}$ mode and the $TE_{01}$ mode may be expressed by Equation 4 presented below:

$$f_{TE10} = \frac{1}{2\pi(\mu\varepsilon\cdot.5)}\sqrt{\left(\frac{\pi}{\text{width}}\right)}$$

$$f_{TE01} = \frac{1}{2\pi(\mu\varepsilon\cdot.5)}\sqrt{\left(\frac{3\pi}{2\text{height}}\right)}$$

Equation 4

In equation 4, $f_{TE10}$ is a transmission signal frequency in the $TE_{10}$ mode, $\mu$ is permeability of the inner medium of the antenna, $\varepsilon$ is permittivity of the inner medium of the antenna, width is a size of the antenna in the width direction, $f_{TE01}$ is a transmission signal frequency in the $TE_{01}$ mode, and height s a size of the antenna in the height direction.

In the embodiment shown in FIG. 3, the cross section of the antenna is expressed as a rectangle. The antenna having the rectangular cross section is an example and, according to various exemplary embodiments of the present invention, the cross section of the antenna may have other shapes. For example, due to a limitation to an installation space in the transmission device, at least one corner may have an angle other than a right angle or the cross section may have a pentagonal shape or hexagonal shape other than the rectangular shape.

Figure 7A:
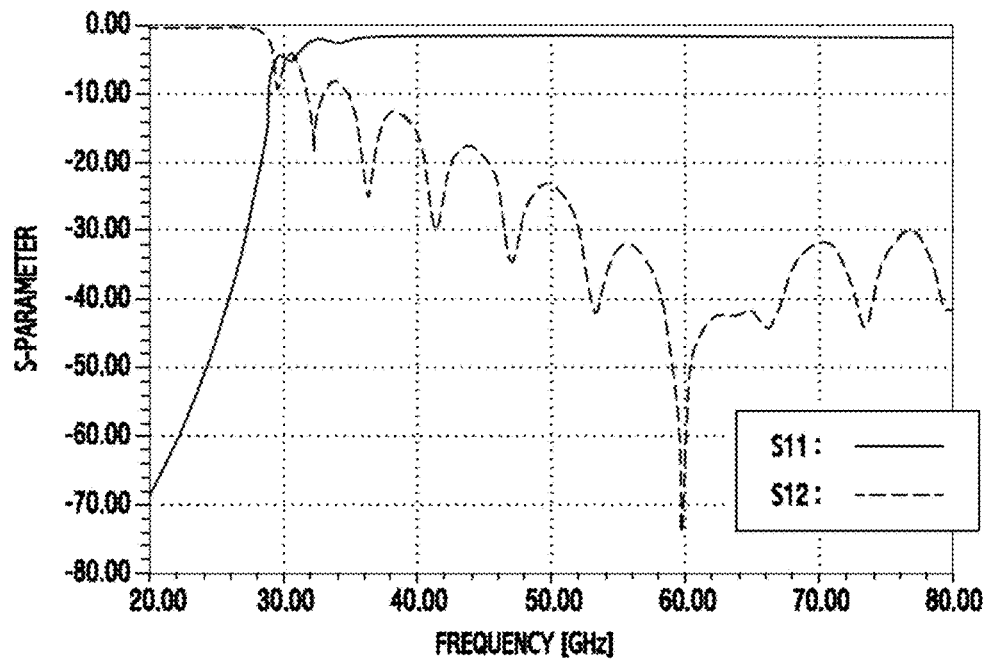
FIGS. 7A and 7B illustrate an S-parameter of the antenna in the transmission device according to an exemplary embodiment of the present invention.
Figure 7B:
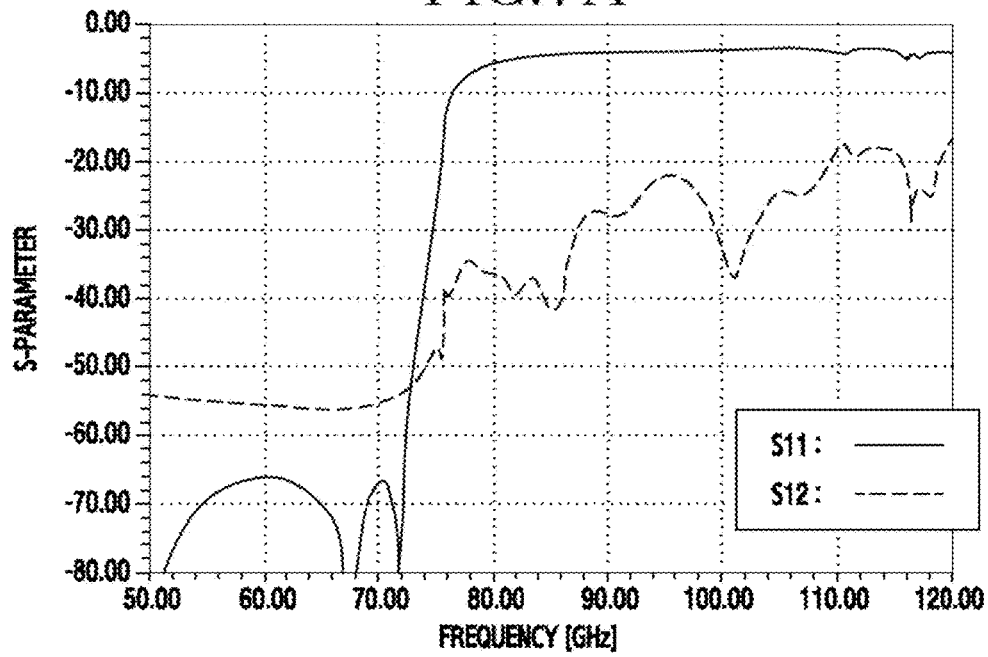

In the $TE_{10}$ mode and the $TE_{01}$ mode, an example of an S-parameter which indicates output power relative to input power of the antenna is as shown in FIGS. 7A and 7B. FIGS. 7A and 7B illustrate an S-parameter of the antenna in the transmission device according to an exemplary embodiment of the present invention. FIG. 7A illustrates an S-parameter according to a frequency in the $TE_{10}$ mode, and FIG. 7B illustrates an S-parameter according to a frequency in the $TE_{01}$ mode. In addition, S11 is a reflection coefficient of an input terminal, and S12 is a reverse transfer coefficient. Referring to FIGS. 7A and 7B, an operation frequency in the $TE_{10}$ mode is about 28 GHz and an operation frequency in the $TE_{01}$ mode is about 73 GHz.

As described above, the antenna according to an exemplary embodiment of the present invention includes the feeding unit and the guiding unit, and has a length, a width, and a height. In addition, the guiding unit includes the plurality of guide elements, and the feeding unit and the guiding unit may be disposed in the dielectric. In addition, at least one surface of the dielectric may be shielded by the conductor and the other surface may be opened.

Figure 8:
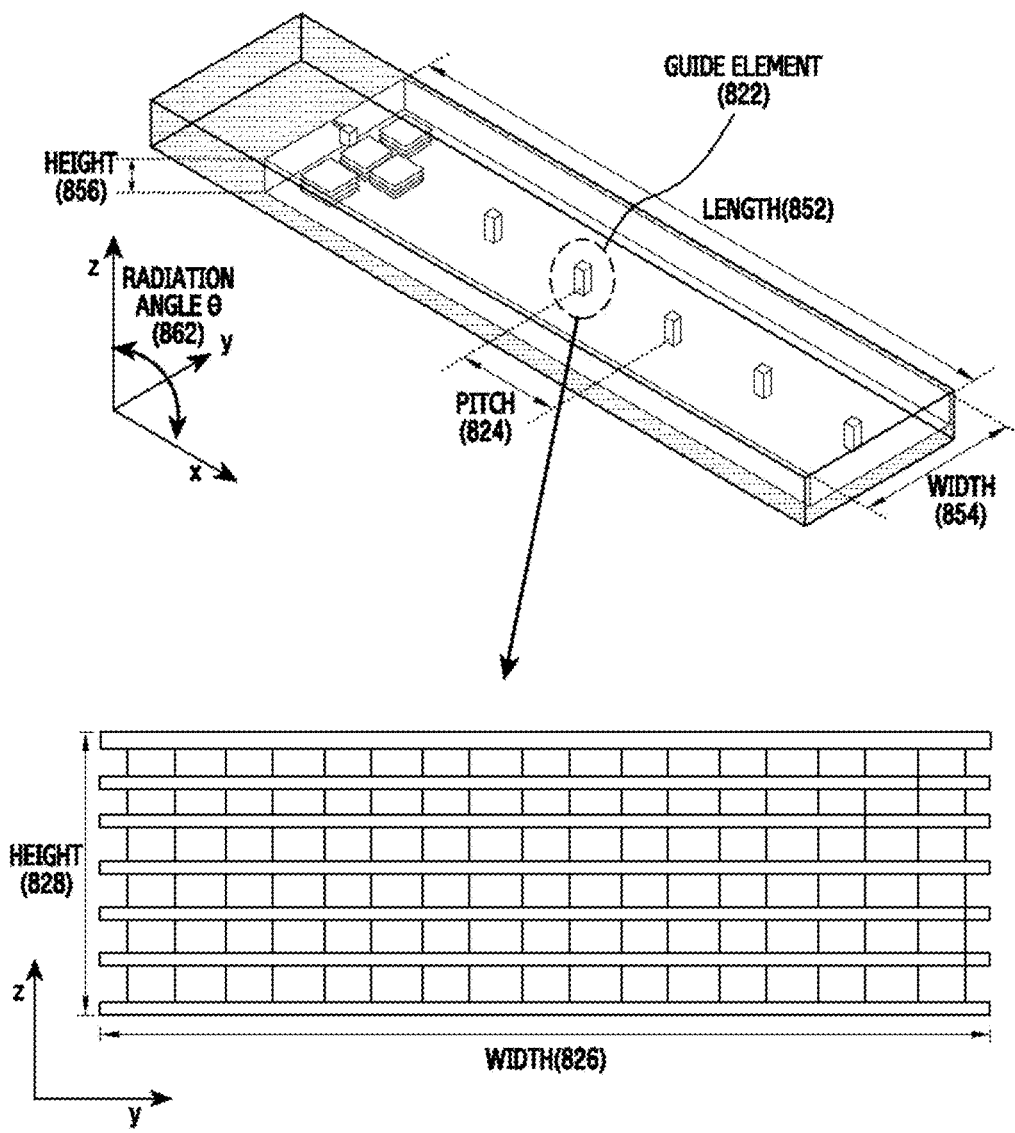
FIG. 8 illustrates design variables for controlling a radiation characteristic of an antenna in a transmission device according to an exemplary embodiment of the present invention.

By adjusting the length, the width, the height, the length of the guiding unit, the distance between the guide elements, the size of each of the guide elements, or the like, different signal radiation patterns may be obtained. Design variables for controlling the signal radiation pattern are as shown in FIG. 8. FIG. 8 illustrates designs variables for controlling a radiation characteristic of an antenna in a transmission device according to an exemplary embodiment of the present invention.

Referring to FIG. 8, individual guide elements 822 forming a guiding unit are arranged at a predetermined distance from one another, and the distance may be referred to as a pitch 824. The guide element 822 may be designed to have a width 826 on the y-axis and a height 828 on the z-axis. The antenna has a length 852 on the x-axis, a width 854 on the y-axis, and a height 856 on the z-axis. In addition, in the following description, a radiation angle θ 862 of a signal is defined on the x-z plane, a direction coinciding with the x-axis is defined as 90° and a direction coinciding with the z-axis is defined as 0°.

Figure 9:
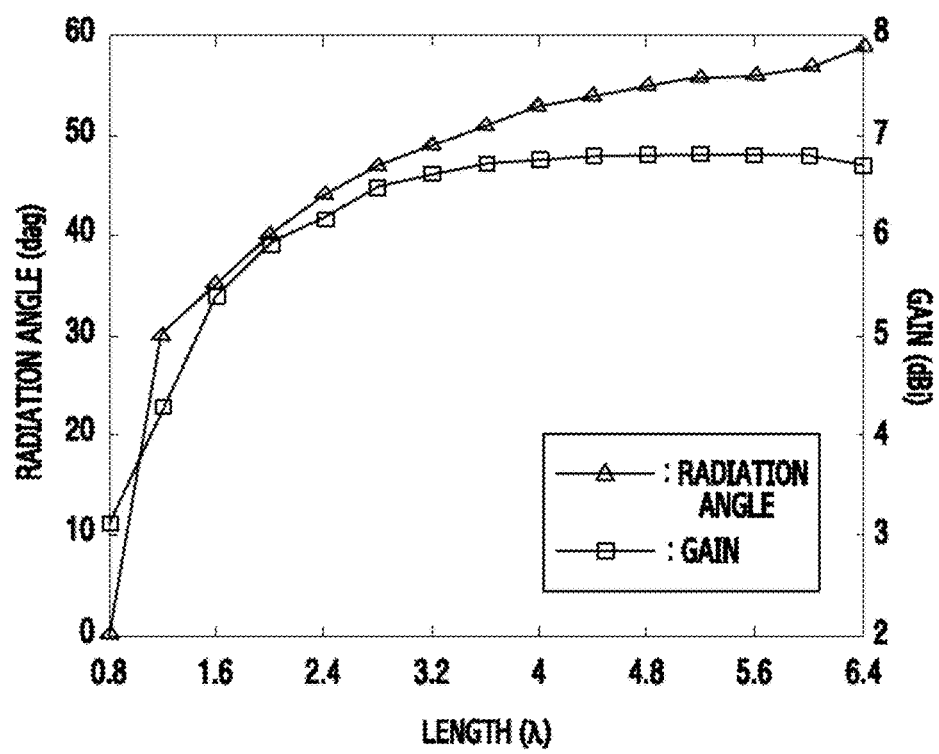
FIG. 9 illustrates radiation characteristics according to a length of the antenna in the transmission device according to an exemplary embodiment of the present invention.

The radiation angle θ 862 may vary according to the length 852. FIG. 9 illustrates radiation characteristics according to the length of the antenna in the transmission device according to an exemplary embodiment of the present invention. In FIG. 9, the horizontal axis indicates the length 852 and the unit is a ratio of the length to a wave length. In FIG. 9, the vertical axis on the left indicates the radiation angle θ 862 and the vertical axis on the right indicates a gain. Referring to FIG. 9, as the length 852 increases, the radiation angle θ 862 increases. That is, as the length 852 decreases, the radiation angle θ 862 is closer to vertical radiation, and, as the length 852 increases, the radiation angle θ 862 is closer to horizontal radiation.

Figure 10:
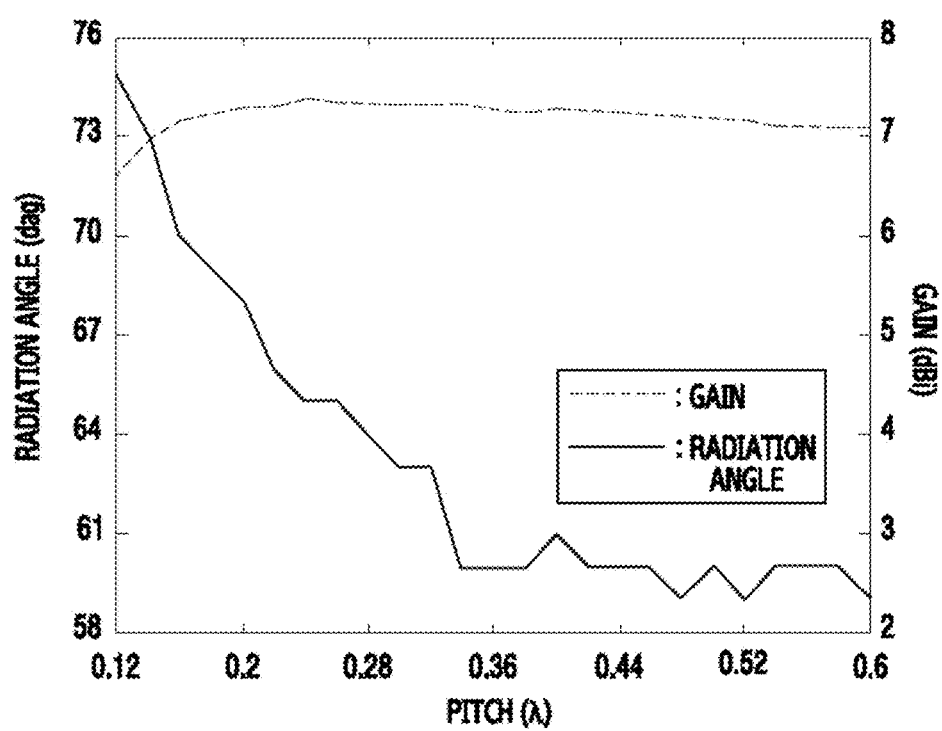
FIG. 10 illustrates radiation characteristics according to a distance between the guide elements of the antenna in the transmission device according to an exemplary embodiment of the present invention.

In addition, the radiation angle θ 862 may vary according to the pitch 824. FIG. 10 illustrates radiation characteristics according to the distance between the guide elements of the antenna in the transmission device according to an exemplary embodiment of the present invention. In FIG. 10, the horizontal axis indicates the pitch 824 and the unit is a ratio of the pitch to a wave length. In FIG. 10, the vertical axis on the left indicates the radiation angle θ 862 and the vertical axis on the right indicates the gain. Referring to FIG. 10, as the pitch 824 increases, the radiation angle θ 862 decreases. Compared to the radiation angle, the gain is not greatly changed.

Figure 11:
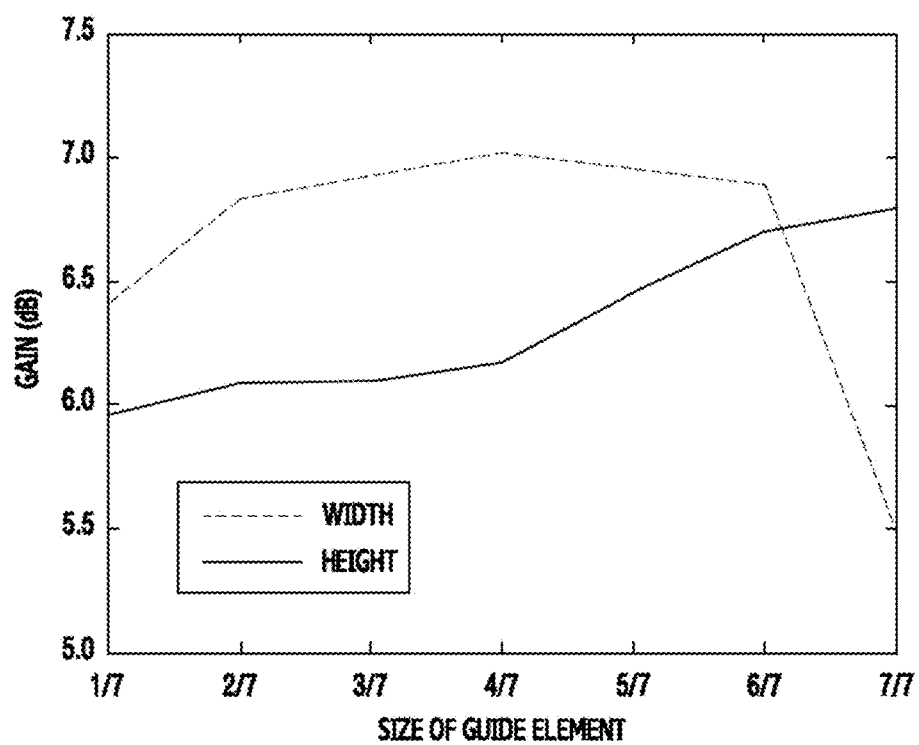
FIG. 11 illustrates a radiation characteristic according to a size of the guide element of the antenna in the transmission device according to an exemplary embodiment of the present invention.

The gain of the antenna may vary according to the size of the guide element 822. FIG. 11 illustrates a radiation characteristic according to the size of the guide element 822 of the antenna in the transmission device according to an exemplary embodiment of the present invention. In FIG. 11, the horizontal axis indicates a ratio of size of the width 826 or the height 828 of the guide element 822 to the total size of the antenna, and the vertical axis indicates a gain. Referring to the graph of the width 826, as the width 826 is closer to 1, the gain increases. However, when the width 826 exceeds 6/7, the gain is reduced. Referring to the graph of the height 828, the gain increases as the height 828 increases.

As described above, the radiation characteristics (for example, the radiation angle, the gain, or the like) may vary according to the length of the antenna, the size of the guide element, the pitch of the guide element, or the like. Accordingly, by adjusting the length of the antenna, the size of the guide element, the pitch of the guide element, or the like, various radiation characteristics may be intended. Furthermore, in the antenna according to an exemplary embodiment of the present invention, the radiation characteristics of the signal may vary according to a direction of a current flowing in the feeding unit. The direction of the current flowing in the feeding unit may vary according to a point of the feeding unit at which the signal is inputted and a direction in which the signal is inputted.

Figure 12A:
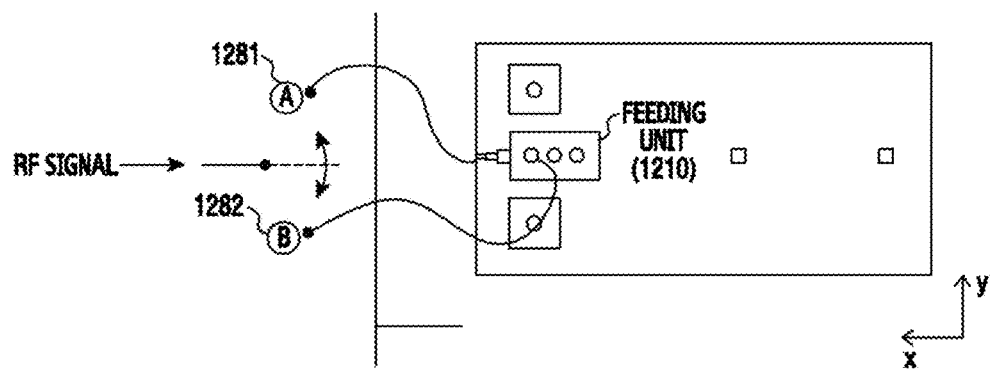
FIGS. 12A and 12B illustrate an example of a structure for controlling a feeding direction of an antenna in a transmission device according to an exemplary embodiment of the present invention.
Figure 12A:
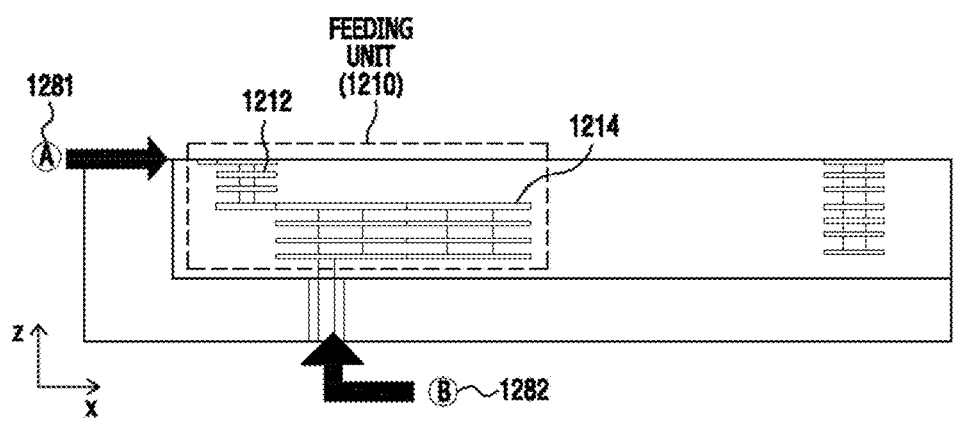
Figure 12B:
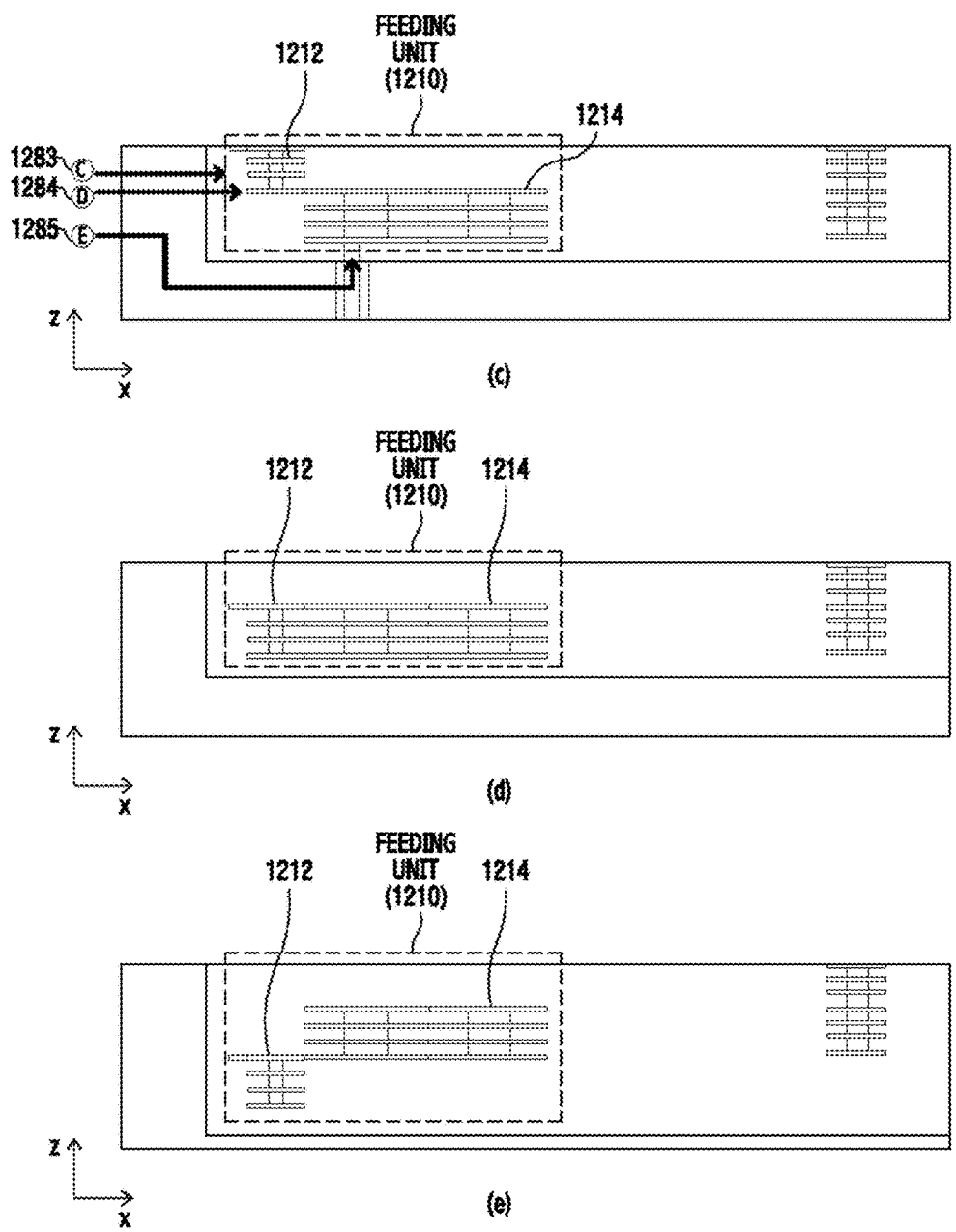

FIGS. 12A and 12B illustrate examples of a structure for controlling a feeding direction of an antenna in a transmission device according to an exemplary embodiment of the present invention. In FIGS. 12A and 12B, view (a) illustrates a conceptual switching structure for providing a signal to a feeding unit 1210, view (b) illustrates signal input points according to a switch connection state, view (c) illustrates other signal input points, and views (d) and (e) illustrate examples of other structures of the feeding unit 1210.

Referring to view (a) of FIG. 12A, an RF signal may be provided to the feeding unit 1210 through an input terminal A 1281 or an input terminal B 1282 through a switch. The switch for selecting the input terminal A 1281 or the input terminal B 1282 may be implemented by using an electronic switch.

Referring to view (b) of FIG. 12A, the feeding unit 1210 includes a first sub unit 1212 and a second sub unit 1214. In the example of view (b) of FIG. 12A, the first sub unit 121 is disposed to be higher than the second sub unit 1214 on the z-axis. When the RF signal is inputted to the input terminal A 1281 disposed on the side surface of the first sub unit 1212, the RF signal is inputted through the upper end of the feeding unit 1210. In this case, the signal may be radiated in an endfire pattern. When the RF signal is inputted to the input terminal B 1282 disposed on the lower end of the second sub unit 1214, the RF signal is inputted through the lower end of the feeding unit 1210. In this case, the signal is radiated in a broadside pattern. According to a radiation pattern of the signal, the input terminal A 1281 may be referred to as an endfire source input and the input terminal B 1282 may be referred to as a broadside source input. A detailed example of the signal radiation pattern according to the RF signal input to the input terminal A 1281 or the input terminal B 1282 is as shown in FIGS. 13 and 14, which will be described below.

Referring to view (c) of FIG. 12B, a signal may be inputted to an input terminal C 1283 or an input terminal D 1284 to be radiated in the endfire pattern. In other words, the signal may be inputted to the input terminal C 1283 disposed on the middle of the side surface of the first sub unit 1212 of the feeding unit 1210. Alternatively, the signal may be inputted to the input terminal D 1284 disposed on the lower end of the side surface of the first sub unit 1212 of the feeding unit 1210. In addition, a signal may be inputted to an input terminal E 1285 to be radiated in the broadside pattern. Similarly to the input terminal B 1282, the input terminal E 1285 may be disposed on the lower end of the second sub unit 1214, but the signal bypasses. That is, the signal inputted to the input terminal E 1285 is initially generated on the side surface of the antenna, but bypasses inside the antenna, thereby being inputted to the lower end of the second sub unit 1214 of the feeding unit 1210.

Views (d) and (e) of FIG. 12B illustrate other arrangements of the first sub unit 1212 and the second sub unit 1214. As shown in view (d) of FIG. 12B, the first sub unit 1212 and the second sub unit 1214 may be disposed on the same location on the z-axis. In addition, as shown in view (e) of FIG. 12B, the first sub unit 1212 may be disposed to be lower than the second sub unit 1214 on the z-axis.

Figure 13A:
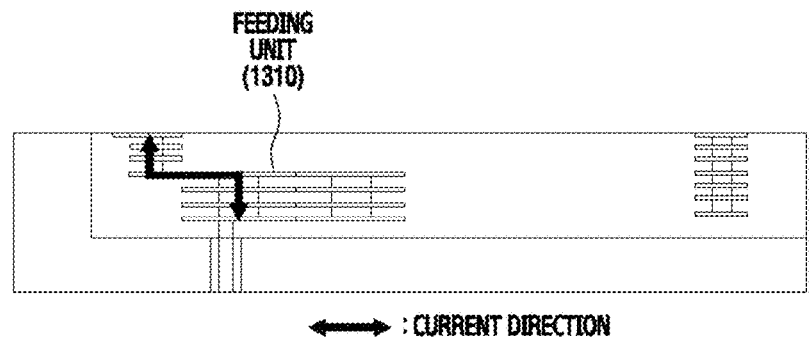
FIGS. 13A and 13B illustrate an example of a radiation characteristic according to a feeding direction of an antenna in a transmission device according to an exemplary embodiment of the present invention.
Figure 13B:
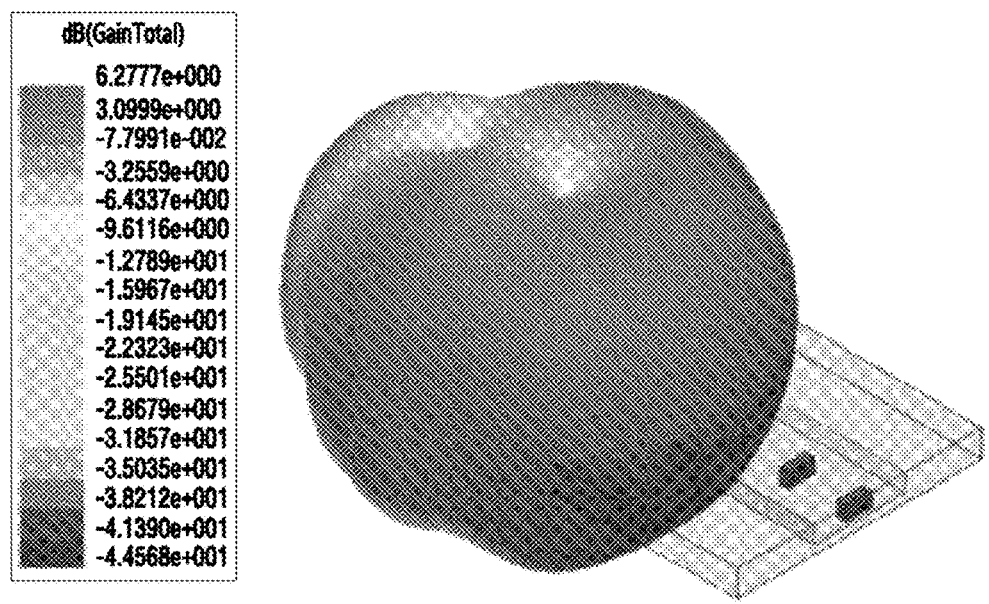

FIGS. 13A and 13B illustrate an example of a radiation characteristic according to a feeding direction of an antenna in a transmission device according to an exemplary embodiment of the present invention. FIG. 13A illustrates a current direction on the feeding unit 1310, and FIG. 13B illustrates an example of a signal radiation pattern according to the current direction as shown in FIG. 7A. When the RF signal is inputted to the input terminal A 1281, the current flows in the vertical direction, that is, in the z-axis direction, as shown in FIG. 7A. In this case, the radiation pattern has directivity in the horizontal direction as shown in FIG. 7B. In the case of FIGS. 13A and 13B, a maximum gain of about 3 dBi or higher may be obtained.

Figure 14A:
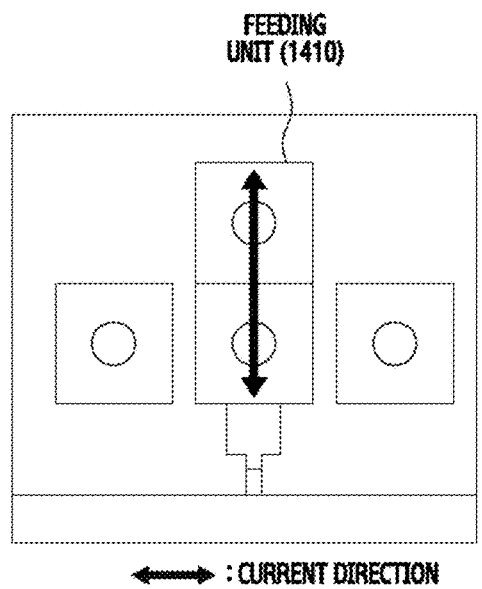
FIGS. 14A and 14B illustrate another example of a radiation characteristic according to a feeding direction of an antenna in a transmission device according to an exemplary embodiment of the present invention.
Figure 14B:
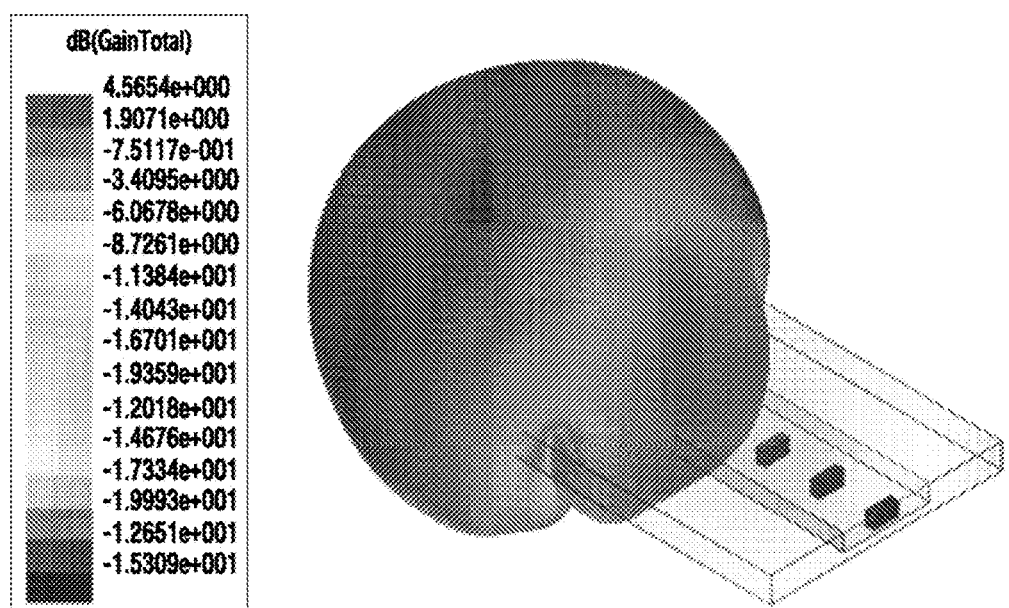

FIGS. 14A and 14B illustrate another example of a radiation characteristic according to a feeding direction of the antenna in the transmission device according to an exemplary embodiment of the present invention. FIG. 14A illustrates a current direction on a feeding unit 1410 and FIG. 14B illustrates an example of a signal radiation pattern according to the current direction as shown in FIG. 14A. When the RF signal is inputted to the input terminal B 1282, the current flows in the horizontal direction, that is, in the x-axis direction, as shown in FIG. 14A. In this case, the radiation pattern has directivity in the vertical direction as shown in FIG. 14B. In the case of FIGS. 14A and 14B, a maximum gain of about 4.56 dBi or higher may be obtained.

The antenna according to various exemplary embodiments of the present invention as described above includes the feeding unit and the guiding unit. According to another exemplary embodiment of the present invention, a plurality of antenna including the feeding unit and the guiding unit described above are arranged, so that the transmission device can support beam steering. For example, a detailed example of a radiation characteristic according to the number of antennas is as shown in FIGS. 15 and 16.

Figure 15:
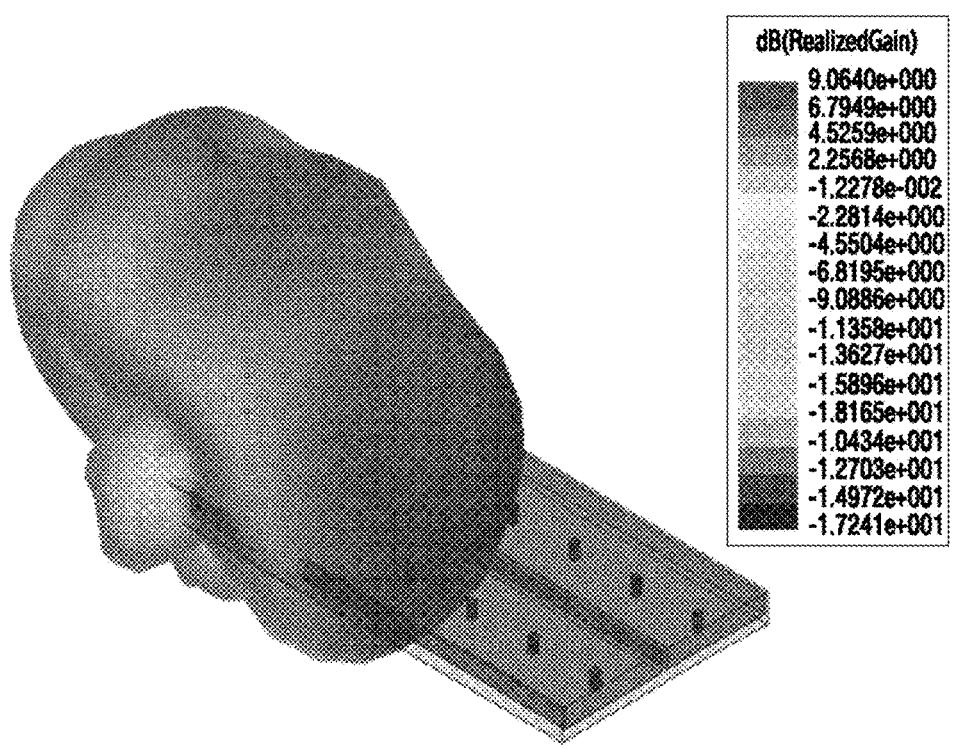
FIG. 15 illustrates an example of a radiation characteristic when two antennas are used in the transmission device according to an exemplary embodiment of the present invention.

FIG. 15 illustrates an example of a radiation characteristic when two antennas are used in the transmission device according to an exemplary embodiment of the present invention. Referring to FIG. 15, two antennas are arranged in parallel. As a result of conducting a simulation, in the case of FIG. 15, a maximum gain of 9.7 dBi appears within a range of a radiation angle from 60° to 70°, and a maximum gain of 6.6 dBi appears at a radiation angle of 90°.

Figure 16:
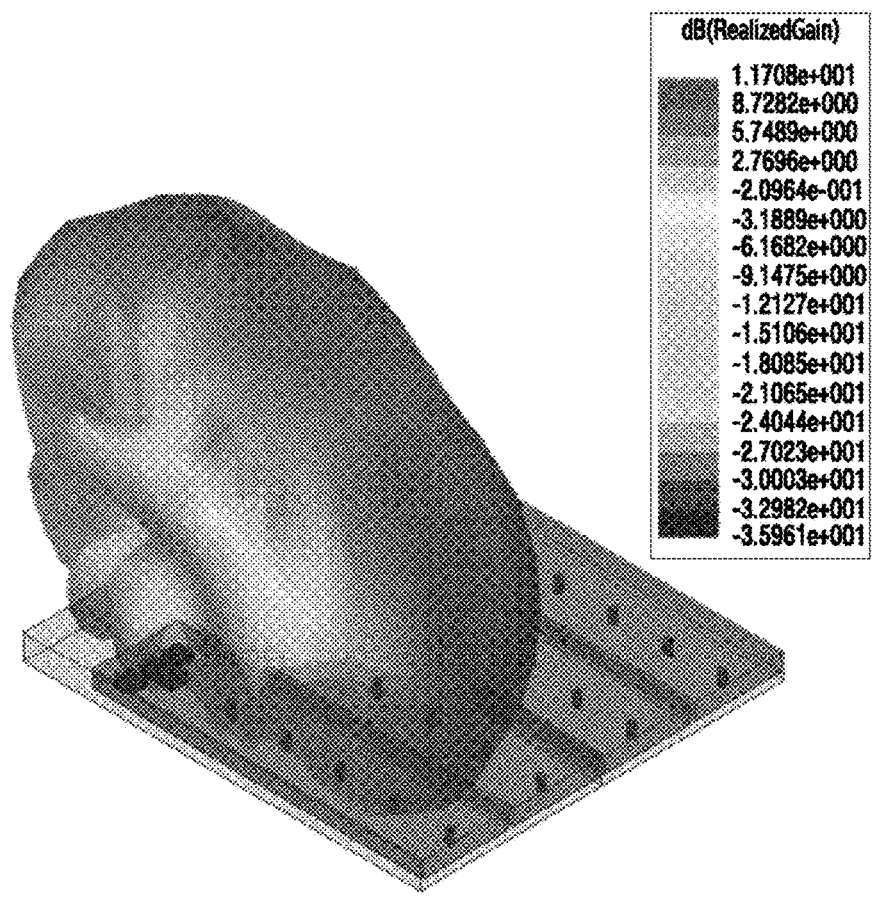
FIG. 16 illustrates an example of a radiation characteristic when four antennas are used in the transmission device according to an exemplary embodiment of the present invention.

FIG. 16 illustrates an example of a radiation characteristic when four antennas are used in the transmission device according to an exemplary embodiment of the present invention. Referring to FIG. 16, four antennas are arranged in parallel. As a result of conducting a simulation, in the case of FIG. 16, a maximum gain of 11.7 dBi appears within a range of a radiation angle from 60° to 70°, and a maximum gain of 8.4 dBi appears at a radiation angle of 90°.

Figure 17A:
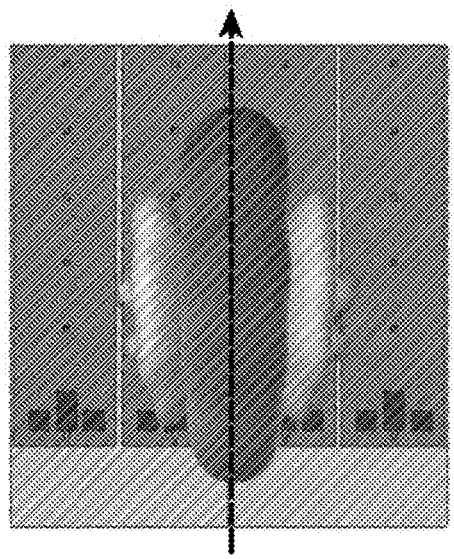
FIGS. 17A, 17B, 17C and 17D illustrate examples of beam steering which uses a plurality of antennas in the transmission device according to an exemplary embodiment of the present invention.
Figure 17B:
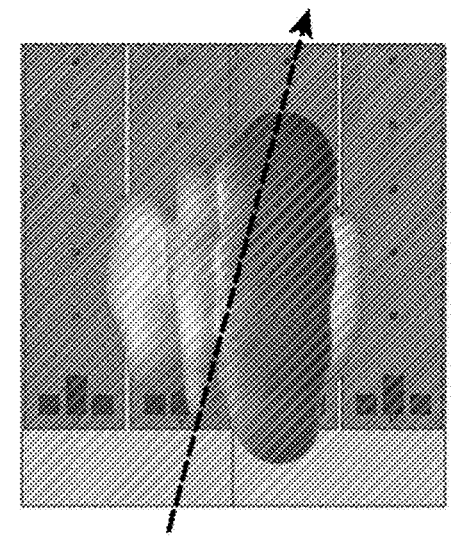
Figure 17C:
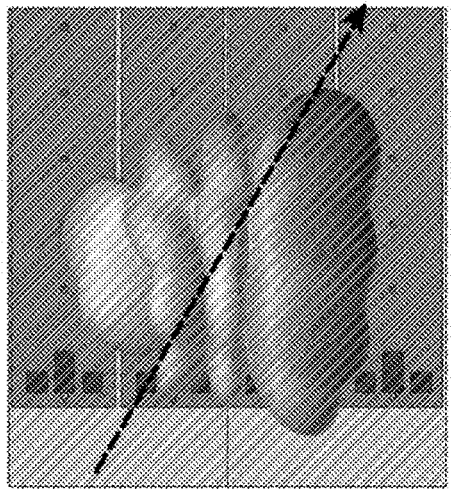
Figure 17D:
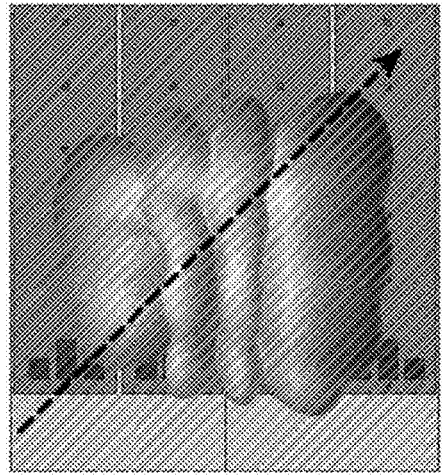

The direction of a beam in the horizontal direction may be controlled by using a plurality of antennas. FIGS. 17A, 17B, 17C and 17C illustrate examples of beam steering which uses a plurality of antennas in the transmission device according to an exemplary embodiment of the present invention. FIGS. 17A, 17B, 17C and 17C illustrate radiation patterns having different directivity on the x-y plane. When the direction of the y-axis is defined as 0°, FIG. 17A illustrates a horizontal radiation angle of 0°, FIG. 17B illustrates a horizontal radiation angle of −15°, FIG. 17C illustrates a horizontal radiation angle of −30°, and FIG. 17D illustrates a horizontal radiation angle of −45°. In the case of FIGS. 17A, 17B, 17C and 17C, according to a result of conducting a simulation, a gain may be obtained according to a vertical radiation angle as follows: in the case of FIG. 17A, a gain of 12.2 dBi is obtained at the vertical radiation angle of 65° and a gain of 8.9 dBi is obtained at the vertical radiation angle of 90°, in the case of FIG. 17B, a gain of 11.87 dBi is obtained at the vertical radiation angle of 65° and a gain of 8.7 dBi is obtained at the vertical radiation angle of 90°, in the case of FIG. 17C, a gain of 11.3 dBi is obtained at the vertical radiation angle of 65° and a gain of 8.3 dBi is obtained at the vertical radiation angle of 90°, and, in the case of FIG. 17D, a gain of 9.7 dBi is obtained at the vertical radiation angle of 65° and a gain of 8.1 dBi is obtained at the vertical radiation angle of 90°.

In the antenna according to the exemplary embodiment of the present invention described above, the guiding unit includes a plurality of guide elements. According to the above-described exemplary embodiments, the guide elements are arranged in a straight line. However, according to another exemplary embodiment of the present invention, the guide elements may be arranged in a nonlinear fashion. For example, the guide elements may be arranged in a circular fashion, a curved line fashion, and a segmental fashion. An example of the nonlinear arrangement is as illustrated in FIGS. 18A and 18B.

Figure 18A:
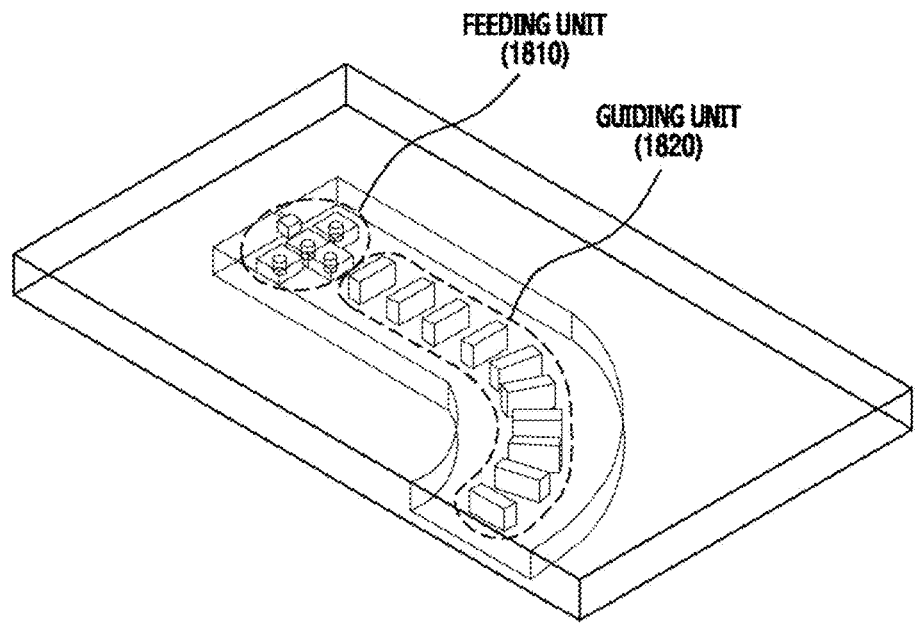
FIGS. 18A and 18B illustrate a configuration example of an antenna in a transmission device according to another exemplary embodiment of the present invention.
Figure 18B:
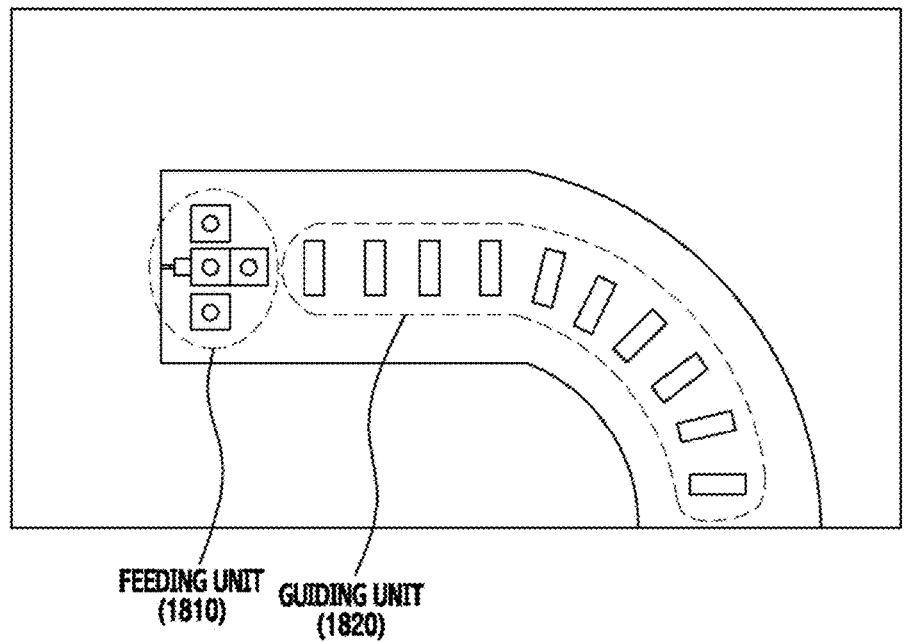

FIGS. 18A and 18B illustrate a configuration example of an antenna in a transmission device according to another exemplary embodiment of the present invention. FIG. 18A illustrates a perspective view and FIG. 18B illustrates a plane view. Referring to FIGS. 18A and 18B, the antenna includes a feeding unit 1810 and a guiding unit 1820. Guide elements of the guiding unit 1820 are arranged in a nonlinear fashion unlike in the case of FIG. 3. In the case of FIGS. 18A and 18B, the guiding unit 1820 is configured in a linear fashion within a predetermined range from the feeding unit 1810. However, according to another exemplary embodiment of the present invention, the entirety of the guiding unit 1820 may be configured in a nonlinear fashion. In addition, in the case of FIGS. 18A and 18B, the guiding unit 1820 may have a curved shape including a bending part in one direction. However, according to another exemplary embodiment of the present invention, the guiding unit 1820 may have a complex curved shape including two or more bending parts.

Figure 19:
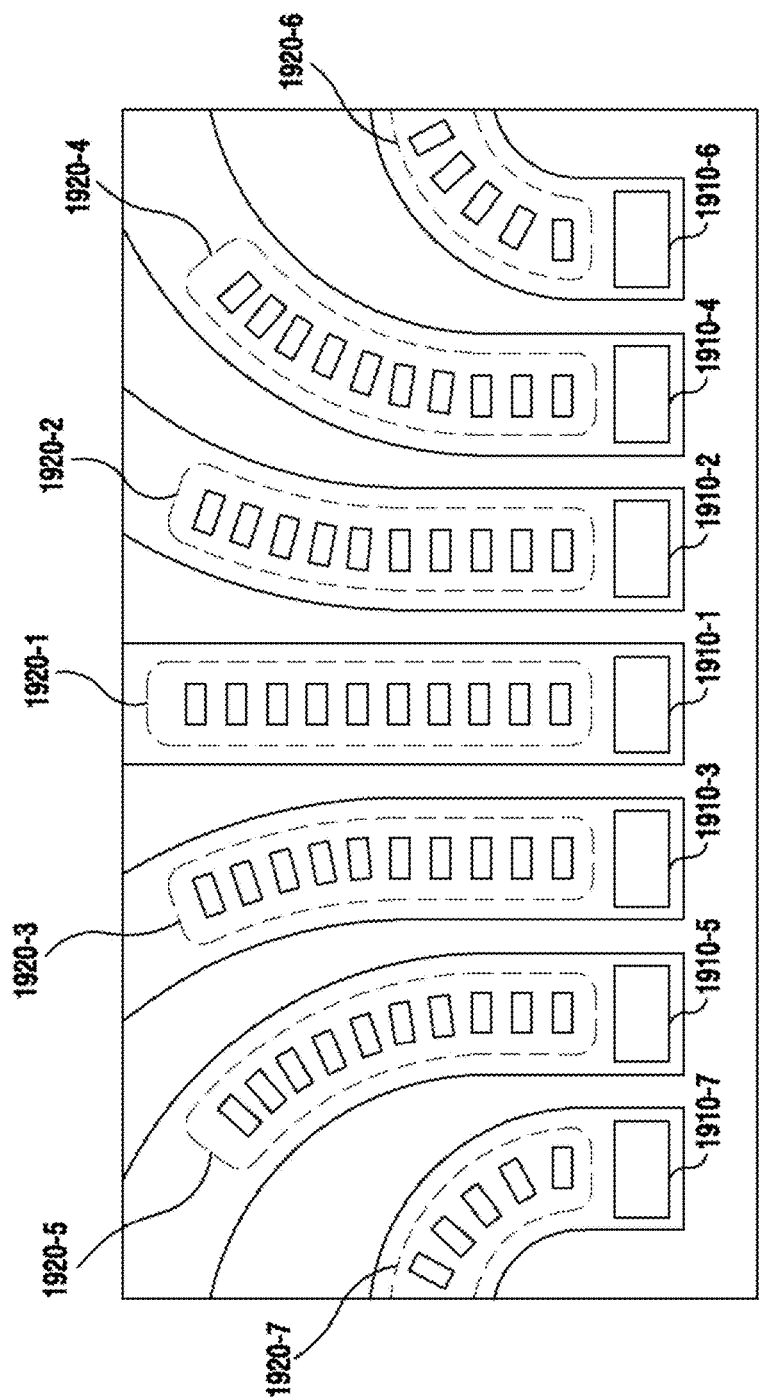
FIG. 19 illustrates a configuration example of an antenna in a transmission device according to another exemplary embodiment of the present invention.

FIG. 19 illustrates a configuration example of an antenna in a transmission device according to another exemplary embodiment of the present invention. FIG. 19 illustrates an example of a configuration of antennas in which linear arrangement and nonlinear arrangement of guide elements are mixed. FIG. 19 illustrates seven antennas. However, according to another exemplary embodiment of the present invention, six or less or eight or more antennas may be configured in a similar fashion.

Referring to FIG. 19, a first antenna includes a feeding unit 1910-1 and a guiding unit 1920-1 which includes guide elements arranged in a linear fashion. A second antenna includes a feeding unit 1910-2 and a guiding unit 1920-2 which includes guide elements arranged in a nonlinear fashion, specifically, in rightward bent fashion. A third antenna includes a feeding unit 1910-3 and a guiding unit 1920-3 which includes guide elements arranged in a nonlinear fashion, specifically, in a leftward bent fashion. Herein, the guiding unit 1920-2 and the guiding unit 1920-3 have the same curvature. A fourth antenna includes a feeding unit 1910-4 and a guiding unit 1920-4 which includes guide elements arranged in a nonlinear fashion, specifically, in a rightward bent fashion. A fifth antenna includes a feeding unit 1910-5 and a guiding unit 1920-5 which includes guide elements arranged in a nonlinear fashion, specifically, in a leftward bent fashion. Herein, the guiding unit 1920-4 and the guiding unit 1920-5 have the same curvature, and the curvature of the guiding unit 1920-4 and the guiding unit 1920-5 is greater than the curvature of the guiding unit 1920-2 and the guiding unit 1920-3. A sixth antenna includes a feeding unit 1910-6 and a guiding unit 1920-6 which includes guide elements arranged in a nonlinear fashion, specifically, in a rightward bent fashion. A seventh antenna includes a feeding unit 1910-7 and a guiding unit 1920-7 which includes guide elements arranged in a nonlinear fashion, specifically, in a leftward bent fashion. Herein, the guiding unit 1920-6 and the guiding unit 1920-7 have the same curvature, and the curvature of the guiding unit 1920-6 and the guiding unit 1920-7 is greater than the curvature of the guiding unit 1920-4 and the guiding unit 1920-5.

Figure 20:
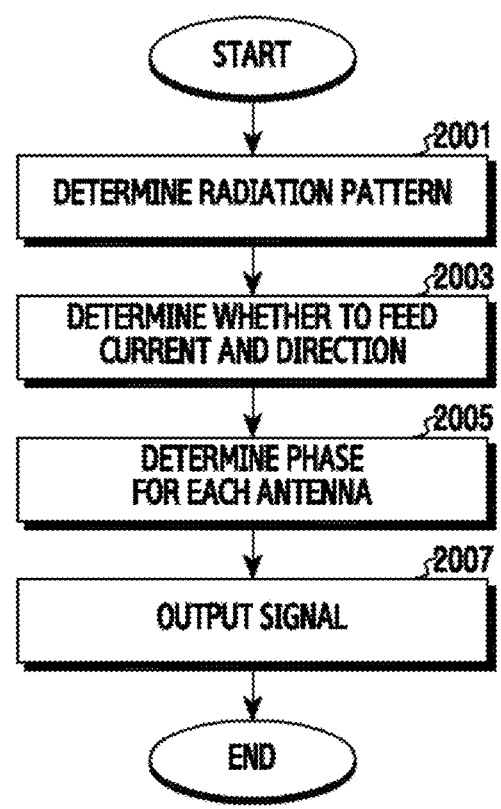
FIG. 20 illustrates a signal transmission procedure in the transmission device according to an exemplary embodiment of the present invention.

FIG. 20 illustrates a signal transmission procedure in the transmission device according to an exemplary embodiment of the present invention. FIG. 20 illustrates an example of a signal transmission method using the antenna according to the above-described various exemplary embodiments. To achieve this, the transmission device may further include at least one processor to control signal transmission.

Referring to FIG. 20, the transmission device determines a radiation pattern in step 2001. The radiation pattern includes at least one of a direction of a beam, a size of a beam, and a beam width. That is, the transmission device determines at least one of the direction of the beam, the size of the beam, and the beam width. For example, the transmission device may determine the radiation pattern for beam sweeping for beam training, or determine the radiation pattern to fix a beam in an optimum beam direction, which is determined through the beam training.

Next, the transmission device proceeds to step 2003 to determine whether to feed a current and a feeding direction. The transmission device includes a plurality of antennas, that is, an antenna array. In this case, the transmission device may control a beam width by controlling the number of antennas to feed a current. In addition, as described above with reference to FIGS. 12A and 12B, a signal is radiated in an endfire pattern or a broadside pattern according to a feeding direction. That is, the transmission device may determine the feeding direction according to the radiation pattern which is determined in step S2001. That is, the feeding direction is related to a beam direction.

Next, the transmission device proceeds to step 2005 to determine a phase for each antenna. That is, the transmission device determines at least one phase for beamforming with respect to the at least one antenna to feed the current. Accordingly, by determining the phase for each antenna, the transmission device may control the direction of the beam, specifically, the angle of the beam. Accordingly, the transmission device determines the phase for each antenna according to the radiation pattern which is determined in step 2001.

Thereafter, the transmission device proceeds to step 2007 to output a signal. That is, the transmission device feeds a current to the at least one antenna which is selected in step 2003. In this case, the transmission device feeds the current in the feeding direction which is determined in step 2003. In addition, the transmission device applies the phase which is determined in step 2005 to the signal which is fed to each antenna. Accordingly, the transmission device may transmit the signal in the radiation pattern which is determined in step 2001. That is, the transmission device adjusts the radiation pattern of the signal through the guiding unit which is formed of a plurality of elements physically spaced from one another.

Figure 21:
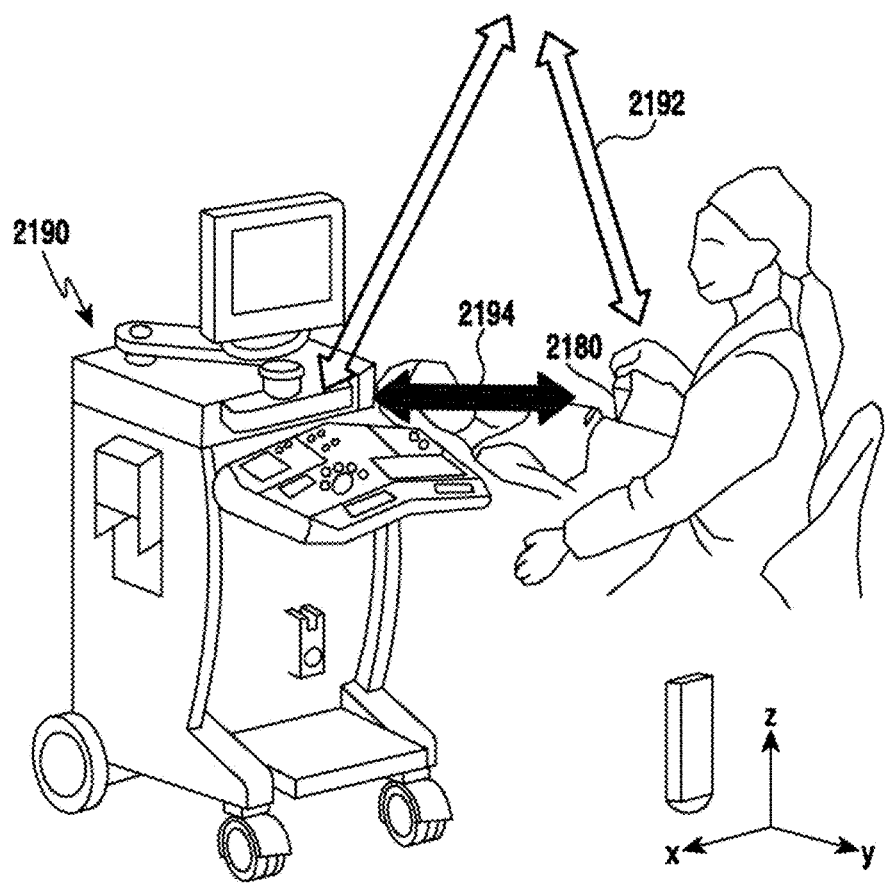
FIG. 21 illustrates an example of utilization of the antenna according to an exemplary embodiment of the present invention.

FIG. 21 illustrates an example of utilization of the antenna according to an exemplary embodiment of the present invention. FIG. 21 illustrates a case in which the antenna according to an exemplary embodiment of the present invention is applied to ultrasonic examination equipment. As shown in FIG. 21, the antenna may be utilized to minimize interruption which may occur between frames forming an ultrasonic image which is transceived between a wireless probe 2180 and an ultrasonic diagnosis device 2190.

In a high frequency band which has strong directivity, the directionality of signal radiation greatly influences a signal quality. Referring to FIG. 21, a signal transceiving direction between the wireless probe 2180 and the ultrasonic diagnosis device 2190 may be divided into a line of sight (LOS) direction 2194 and a non line of sight (NLOS) direction 2192. Referring to FIG. 21, the wireless probe 2180 is normally used with the ultrasonic diagnosis device 2190 being placed in a direction perpendicular to a major axis (for example, the x-axis). Accordingly, in order to transceive signals in the LOS direction 2194, a signal should be radiated in a direction perpendicular to the major axis (for example, the x-axis) of the wireless probe 2180. In addition, in order to transceive signals in the NLOS direction 2194, a signal should be radiated in a direction similar to the major axis (for example, the x-axis) of the wireless probe 2180. Herein, the NLOS refers to a path through which signals are reflected on other objects (for example, a wall, a ceiling, or the like) and are transceived.

Figures 22A, 22B:
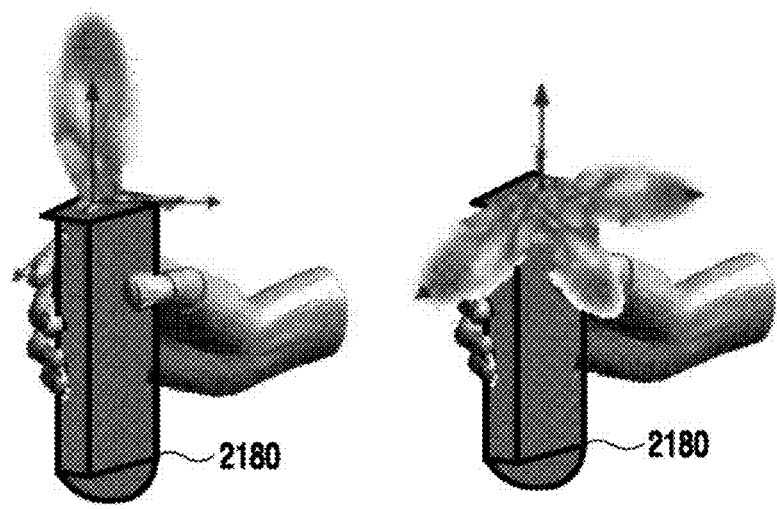
FIGS. 22A and 22B illustrate radiation patterns of a wireless probe to which the antenna is applied according to an exemplary embodiment of the present invention.

FIGS. 22A and 22B illustrate radiation patterns of a wireless probe to which the antenna according to an exemplary embodiment of the present invention is applied. FIGS. 22A and 22B illustrate examples of signal radiation patterns for communication in the LOS direction 2194 and the NLOS direction 2192 in the wireless probe 2180.

Referring to FIG. 22A, a signal is radiated in the direction of the major axis (for example, the z-axis) of the wireless probe 2180 to perform communication in the NLOS direction 2192. To achieve this, a signal for radiation in the broadside direction may be inputted to the feeding unit of the antenna. Referring to FIG. 22B, a signal is radiated in the direction perpendicular to the major axis (for example, the z-axis) of the wireless probe 2180 to perform communication in the LOS direction 2194. To achieve this, a signal for radiation in the endfire direction may be inputted to the feeding unit of the antenna. In this case, it is preferable that the antenna is mounted on the uppermost end of the wireless probe 2180 to prevent signal radiation from being interfered by user's hand in consideration of a normal using method of the wireless probe 2180.

Figure 23A:
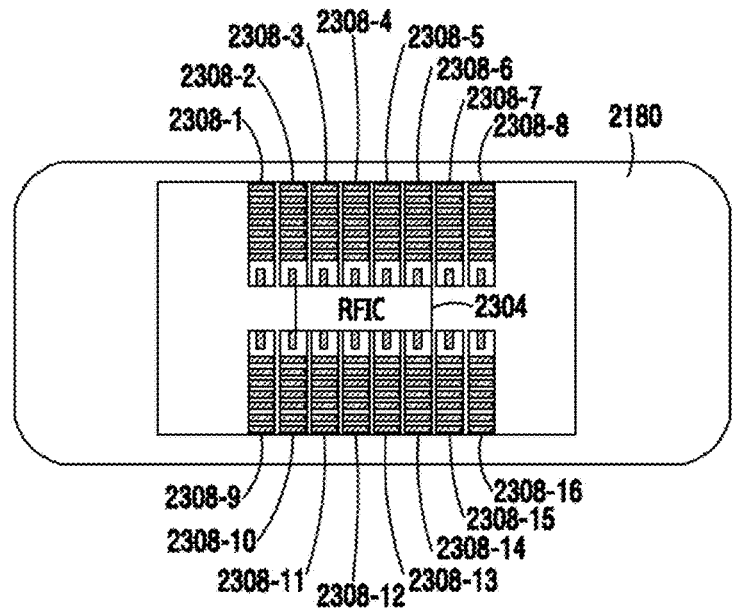
FIGS. 23A and 23B illustrate arrangement of antennas installed in a wireless probe according to an exemplary embodiment of the present invention.
Figure 23B:
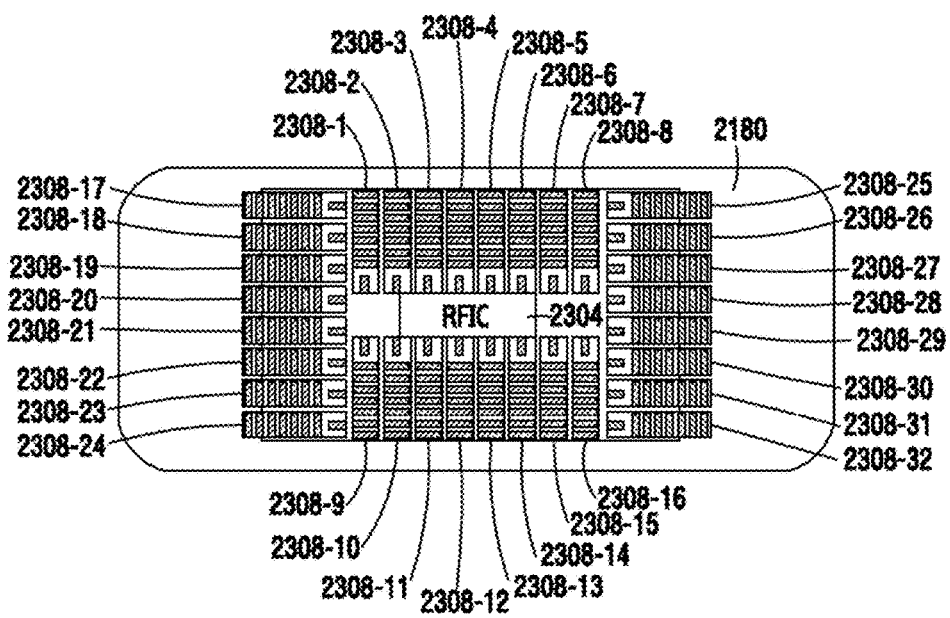

FIGS. 23A and 23B illustrate arrangement of antennas installed in a wireless probe according to an exemplary embodiment of the present invention. FIGS. 23A and 23B illustrate a circuit including an RFIC 2304 and a plurality of antennas 2308. The circuit shown in FIGS. 23A and 23B may be disposed at the upper end of the wireless probe 2180.

Referring to FIG. 23A, the circuit including the RFIC 2304 and antennas 2308-1 to 2308-16 may be disposed perpendicular to the major axis (for example, the z-axis) of the wireless probe 2180. This arrangement makes it possible to transceive signals in the broadside and endfire directions. Specifically, as shown in FIG. 23A, the antennas 2308-1 to 2308-16 may be divided into two antenna groups which are arranged in different directions with reference to the RFIC 2304. The antenna groups arranged in different directions may be selectively used according to a relative location relationship between the ultrasonic diagnosis device 2190 and the wireless probe 2180. For example, when the ultrasonic diagnosis device 2190 is located on the left of the user who uses the wireless probe 2180 with user's right hand, the antenna group which is close to the ultrasonic diagnosis device 2190 may be used.

Referring to FIG. 23B, the circuit including the RFIC 2304 and antennas 2308-1 to 2308-32 may be disposed perpendicular to the major axis (for example, the z-axis) of the wireless probe 2180. This arrangement makes it possible to transceive signals in the broadside and endfire directions. Specifically, the antennas 2308-1 to 2308-32 may be divided into four antenna groups which are arranged in different directions with reference to the RFIC 2304. The antenna groups arranged in different directions may be selectively used according to a relative location relationship between the ultrasonic diagnosis device 2190 and the wireless probe 2180. For example, the antenna group which is close to the ultrasonic diagnosis device 2190 may be used.

FIG. 23A illustrates an example of two antenna groups for two directions, and FIG. 23B illustrates an example of four antenna groups for four directions. However, the present invention is not limited to two or four directions. That is, according to another exemplary embodiment of the present invention, only one direction may be considered or three directions may be considered, or an antenna structure for five or more directions may be included in the wireless probe 2180.

Figure 24:
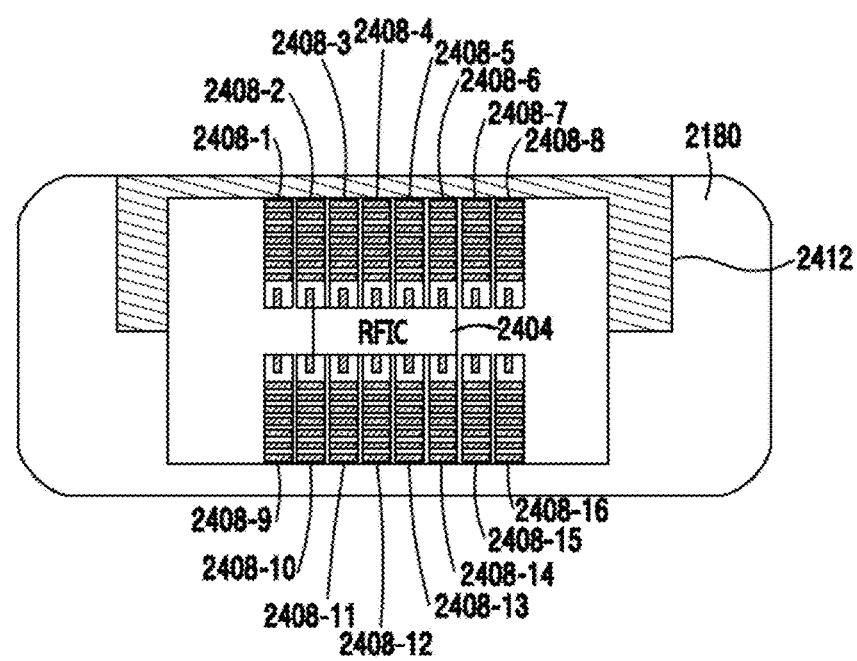
FIG. 24 illustrates arrangement of antennas installed in a wireless probe with a heat sink plate according to an exemplary embodiment of the present invention.

FIG. 24 illustrates arrangement of antennas installed in a wireless probe with a heat sink plate according to an exemplary embodiment of the present invention. FIG. 24 illustrates a circuit including an RFIC 2404 and a plurality of antennas 2408-1 to 2408-16. The circuit shown in FIG. 24 may be located at the upper end of the wireless probe 2180. Referring to FIG. 24, in addition to the RFIC 2404 and the antennas 2408-1 to 2408-16, a heat sink plate 2412 may be installed. The heat sink plate 2412 performs a function of discharging heat generated in the RFIC 2404 and the antennas 2408-1 to 2408-16 to the outside. FIG. 24 illustrates a case in which the heat sink plate 2412 is added to the structure shown in FIG. 23A. However, the heat sink plate 2412 may be added to other antenna structures (for example, FIG. 23B).

In the above-described exemplary embodiments of the present invention, the components included in the present invention are expressed in singular forms or plural forms according to a detailed exemplary embodiment. However, the singular or plural expression is appropriately selected according to a suggested situation for the convenience of explanation, and the present invention is not limited to the singular or plural components. A component expressed in the plural form may be configured as a single component or a component expressed in the singular form may be configured as a plurality of component.

While specific embodiments have been described in the detailed descriptions of the present invention, various changes can be made within a limit without departing from the scope of the present invention. Therefore, the scope of the present invention should not be limited to and defined by the above-described exemplary embodiments, and should be defined not only by the appended claims but also by the equivalents to the scopes of the claims.

What is claimed is:

1. An apparatus for signal radiation, the apparatus comprising:
    a feeding unit configured to radiate a signal received from a radio frequency (RF) processor; and
    a guiding unit, comprising a plurality of elements physically spaced from one another, configured to adjust a radiation pattern of the signal radiated by the feeding unit,
    wherein the feeding unit and the guiding unit are disposed in a dielectric,
    wherein a surface of the dielectric is opened, and
    wherein the elements of the guiding unit are exposed to the outside of the dielectric through the opened surface.

2. The apparatus of claim 1, wherein the guiding unit is configured to generate at least one radio wave in a transverse electric (TE) mode.

3. The apparatus of claim 1, wherein the feeding unit is configured to receive, from the RF processor, the signal without a transmission line or through a transmission line having a length that is shorter than a threshold.

4. The apparatus of claim 1,
wherein at least one of surfaces are parallel to an array that the elements are disposed in the guiding unit.

5. The apparatus of claim 1, wherein the radiation pattern is adjusted according to at least one of a length of the dielectric comprising the feeding unit and the guiding unit, a distance between each of the elements of the guiding unit, and a size of each of the elements.

6. The apparatus of claim 5, wherein the radiation pattern comprises at least one of a radiation angle.

7. The apparatus of claim 6, wherein the radiation angle is adjusted according to the length of the dielectric.

8. The apparatus of claim 6, wherein the radiation angle is adjusted according to the distance between the elements of the guiding unit.

9. The apparatus of claim 6, wherein the gain is adjusted according to the size of the each of the elements.

10. The apparatus of claim 1,
wherein the radiation pattern has one of horizontal directivity and vertical directivity according to a direction of a current flowing in the feeding unit, and
the direction of the current is determined based on a point of the feeding unit at which the signal is inputted.

11. The apparatus of claim 1, wherein the feeding unit comprises a plurality of input paths corresponding to an input point of the signal.

12. The apparatus of claim 11, wherein the feeding unit further comprises a plurality of switches configured to provide the signal to one of the plurality of the input paths.

13. The apparatus of claim 1, wherein the guiding unit comprises a plurality of elements that are linearly arranged.

14. The apparatus of claim 1, wherein the guiding unit comprises a plurality of elements that are nonlinearly arranged.

15. The apparatus of claim 1,
wherein the feeding unit comprises a plurality of sub units, and
wherein at least one sub unit among the plurality of the sub units is disposed to be higher or lower than other sub units to adjust the radiation pattern.

16. A method for operating of a transmission device, the method comprising:
radiating, by a feeding unit, a signal received from a radio frequency (RF) processor; and
adjusting, by a guiding unit, a radiation pattern of the signal,
wherein the guiding unit comprises a plurality of elements physically spaced from one another,
wherein the feeding unit and the guiding unit are disposed in a dielectric,
wherein a surface of the dielectric is opened, and
wherein the elements of the guiding unit are exposed to the outside of the dielectric through the opened surface.

17. The method of claim 16, wherein the radiation pattern comprises at least one of a direction of a beam, a size of a beam, and a beam width.

18. The method of claim 16, further comprising:
determining a number of at least one antenna to feed a current according to a beam width.

19. The method of claim 16, further comprising:
determining a feeding direction of at least one antenna according to a beam direction.

20. The method of claim 16, further comprising:
determining a phase of the signal to be inputted to at least one antenna according to a beam direction.

* * * * *